US007977381B2

(12) United States Patent  
Kay et al.

(10) Patent No.: US 7,977,381 B2
(45) Date of Patent: Jul. 12, 2011

(54) PLATINUM COMPLEXES AND METHODS FOR INHIBITING TUMOR CELL PROLIFERATION

(75) Inventors: Heidi Kay, Wesley Chapel, FL (US); Jay W. Palmer, Sun City Center, FL (US); Joseph A. Stanko, Temple Terrace, FL (US); Said M. Sebti, Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 11/703,497

(22) Filed: Feb. 7, 2007

(65) Prior Publication Data

US 2007/0161613 A1 Jul. 12, 2007

Related U.S. Application Data

(63) Continuation of application No. 11/030,567, filed on Jan. 6, 2005, now abandoned.

(60) Provisional application No. 60/534,575, filed on Jan. 6, 2004.

(51) Int. Cl.
*C07F 15/00* (2006.01)

(52) U.S. Cl. ............ 514/492; 514/184; 544/225; 546/2; 548/101; 556/136; 556/137

(58) Field of Classification Search .................. 514/184, 514/492; 544/225; 546/2; 548/101; 556/136, 556/137
See application file for complete search history.

(56) References Cited

U.S. PATENT DOCUMENTS

| 3,904,663 | A | 9/1975 | Tobe et al. |
| 4,177,263 | A | 12/1979 | Rosenberg et al. |
| 5,849,790 | A * | 12/1998 | Palmer et al. .................. 514/492 |
| 5,998,648 | A | 12/1999 | Sohn et al. |
| 7,238,372 | B2 | 7/2007 | Turkson et al. |
| 7,754,684 | B2 | 7/2010 | Stewart et al. |
| 2002/0035243 | A1 | 3/2002 | Imfeld et al. |
| 2002/0120100 | A1 | 8/2002 | Bonny |
| 2003/0032594 | A1 | 2/2003 | Bonny |
| 2004/0175369 | A1 | 9/2004 | Yu et al. |
| 2005/0074502 | A1 | 4/2005 | Turkson et al. |
| 2005/0080131 | A1 | 4/2005 | Kay et al. |
| 2009/0214626 | A1 | 8/2009 | Kay et al. |
| 2010/0190180 | A1 | 7/2010 | Kay |

FOREIGN PATENT DOCUMENTS

| EP | 0328274 A1 | 8/1989 |
| EP | 0812852 A1 | 12/1997 |
| JP | H08-176175 A2 | 7/1996 |
| WO | WO 96/26949 A1 | 9/1996 |
| WO | WO 2005/016946 A3 | 2/2005 |
| WO | WO 2005/023824 A3 | 3/2005 |

OTHER PUBLICATIONS

PLATINOL-AQ (cisplatin injection) package insert. Revised Apr. 2006.* www.cancer.gov/cancertopics/alphalist accessed Jul. 15, 2008.*
Cleare et al. "Antitumor platinum compounds Relation between structure and activity" Platinum Metals Review (1973), 17(1), 2-13.*
Akira, S. "Roles of STAT3 Defined by Tissue-Specific Gene Targeting", *Oncogene*, 2000, pp. 2607-2611, vol. 19.
Ardizzoni, A. et al. "The Combination of Etoposide and Cisplatin in Non-Small-Cell Lung Cancer (NSCLC)", *Ann. Oncol.*, 1999, pp. S13-S17, vol. 10.
Bowman, T. et al. "STATs in Oncogenesis", *Oncogene*, 2000, pp. 2474-2488, vol. 19.
Bowman, T. et al. "Stat3-Mediated Myc Expression is Required for Src Transformation and PDGF-Induced Mitogenesis", *Proc Natl. Acad. Sci. USA*, 2000, pp. 7319-7324, vol. 98, No. 3.
Bromberg, J. F. et al. "Transcriptionally Active Stat1 is Required for the Antiproliferative Effects of Both Interferon Alpha and Interferon Gamma", *Proc. Natl. Acad. Sci. USA*, 1996, pp. 7673-7678, vol. 93.
Bromberg, J. F. et al. "Stat3 Activation is Required for Cellular Transformation by V-src", *Mol. Cell. Biol.*, 1998, pp. 2553-2558, vol. 18, No. 5.
Bromberg, J. F. et al. "Stat3 as an Oncogene", *Cell*, 1999, pp. 295-303, vol. 98.
Catlett-Falcone, R. et al. "Constitutive Activation of Stat3 Signaling Confers Resistance to Apoptosis in Human U266 Myeloma Cells", *Immunity*, 1999, pp. 105-115, vol. 10.
Catlett-Falcone, R. et al. "STAT Proteins as Novel Targets for Cancer Therapy", *Curr. Opin. Oncol.*, 1999, pp. 490-496, vol. 11.
Chernyaev et al. Zhurnal Neorganicheskoi Khimii, 1966, pp. 1365-1373, vol. 11, XP009041845.
Coffer, P. J. et al. "The Role of STATs in Myeloid Differentiation and Leukemia", *Oncogene*, 2000, pp. 2511-2522, vol. 19.
Cuny, G.D. et al. "Photoactivated Virucidal Properties of Tridentate 2,2'-Dihydroxy Azobenzene and 2-Salicylideneaminophenol Platinum Pyridine Complexes", *Bioorganic & Medicinal Chemistry Letters*, 1999, pp. 237-240, vol. 9.
Darnell, J. E., Jr. et al. "Jak-STAT Pathways and Transcriptional Activation in Response to IFNs and Other Extracellular Signaling Proteins", *Science*, 1994, pp. 1415-1421, vol. 264, No. 5164.
Darnell, J. E., Jr. "STATs and Gene Regulation", *Science*, 1997, pp. 1630-1635, vol. 277.
Epling-Burnette, P. K. et al. "Inhibition of STAT3 Signaling Leads to Apoptosis of Leukemic Large Granular Lymphocytes and Decreased Mcl-1 Expression", *J. Clin. Invest*, 2001, pp. 351-361, vol. 107, No. 3.
Fukada, T. et al. "Two Signals are Necessary for Cell Proliferation Induced by a Cytokine Receptor gp130: Involvement of STAT3 in Anti-Apoptosis", *Immunity*, 1996, pp. 449-460, vol. 5.
Garcia, R. et al. "Constitutive Activation of Stat3 in Fibroblasts Transformed by Diverse Oncoproteins and in Breast Carcinoma Cells", *Cell Growth Diff.*, 1997, pp. 1267-1276, vol. 8.

(Continued)

*Primary Examiner* — Joseph R Kosack
(74) *Attorney, Agent, or Firm* — Saliwanchik, Lloyd & Eisenschenk

(57) ABSTRACT

The subject invention concerns platinum complexes that exhibit antitumor cell and/or antiparasitic activity. The subject invention also concerns the use of platinum complexes of the invention to treat oncological and inflammatory disorders. The platinum complexes of the invention can also be used to treat or prevent infection by a virus or a bacterial or parasitic organism in vivo or in vitro.

20 Claims, No Drawings

OTHER PUBLICATIONS

Garcia, R. et al. "Activation of STAT Transcription Factors in Oncogenic Tyrosine Kinase Signaling", *J. Biomed. Sci.*, 1998, pp. 79-85, vol. 5.

Garcia, R. et al. "Constitutive Activation of Stat3 by the Src and JAK Tyrosine Kinases Participates in Growth Regulation of Human Breast Carcinoma Cells", *Oncogene*, 2001, pp. 2499-2513, vol. 20.

Gouilleux, F. et al. "Prolactin and Interleukin-2 Receptors in T Lymphocytes Signal Through a MGF-STAT5-like Transcription Factor", *Endocrinology*, 1995, pp. 5700-5708, vol. 136, No. 12.

Grandis, J. R. et al. "Requirement of Stat3 but Not Stat1 Activation for Epidermal Growth Factor Receptor-Mediated Cell Growth In Vitro", *J. Clin. Invest.*, 1998, pp. 1385-1392, vol. 102, No. 7.

Grandis, J. R. et al. "Constitutive Activation of Stat3 Signaling Abrogates Apoptosis in Squamous Cell Carcinogenesis In Vivo", *Proc. Natl. Acad. Sci. USA*, 2000, pp. 4227-4232, vol. 97, No. 8.

Grandis, J. R. et al. "Epidermal Growth Factor Receptor—Mediated Stat3 Signaling Blocks Apoptosis in Head and Neck Cancer", *Laryngoscope*, 2000, pp. 868-874, vol. 110.

Hirano, T. et al. "Roles of STAT3 in Mediating the Cell Growth, Differentiation and Survival Signals Relayed Through the IL-6 Family of Cytokine Receptors", *Oncogene*, 2000, pp. 2548-2556, vol. 19.

Horiguchi, A. et al. "STAT3, but Not ERKs, Mediates the IL-6-Induced Proliferation of Renal Cancer Cells, ACHN and 769P", *Kidney Int*, 2002, pp. 926-938, vol. 61.

Johnson, P. J. et al. "Overexpressed pp60$^{c\text{-}src}$ Can Induce Focus Formation Without Complete Transformation of NIH 3T3 Cells", *Mol. Cell. Biol.*, 1985, pp. 1073-1083, vol. 5, No. 5.

Kotenko, S. V. et al. "Jak-Stat Signal Transduction Pathway Through the Eyes of Cytokine Class II Receptor Complexes", *Oncogene*, 2000, pp. 2557-2565, vol. 19.

Kunisada, K. et al. "Activation of gp130 Transduces Hypertrophic Signals Via STAT3 in Cardiac Myocytes", *Circulation*, 1998, pp. 346-352, vol. 98.

Le Postollec "Spectres de vibration et struture de composes de coordination nitres du platine IV" *Journal de La Chimie Physique et de Physico-Chime Biologique*, 1965, pp. 67-72, vol. 62, XP009041900.

Lin, T. S. et al. "STAT Signaling in the Pathogenesis and Treatment of Leukemias", *Oncogene*, 2000, pp. 2496-2504, vol. 19.

Muraveiskaya et al. Zhurnal Neorganicheskoi Khimii, 1971, pp. 1643-1649, vol. 16, XP009041849.

Muravenskaya et al. Koordinatsionnaya Khimiya, 1975, pp. 779-790, vol. 1, XP009041867.

Nielsen, M. et al. "Constitutive Activation of a Slowly Migrating Isoform of Stat3 in Mycosis Fungoides: Tyrphostin AG490 Inhibits Stat3 Activation and Growth of Mycosis Fungoides Tumor Cell Lines", *Proc. Natl. Acad. Sci. USA*, 1997, pp. 6764-6769, vol. 94.

Nielsen, M. et al. "Inhibition of Constitutively Activated Stat3 Correlates with Altered Bcl-2/Bax Expression and Induction of Apoptosis in Mycosis Fungoides Tumor Cells", *Leukemia*, 1999, pp. 735-738, vol. 13.

Nitiss, J. L. "A Copper Connection to the Uptake of Platinum Anticancer Drugs", *Proc. Natl. Acad. Sci. USA*, 2002, pp. 13963-13965, vol. 99, No. 22.

Persons, D. L. et al. "Cisplatin-Induced Activation of Mitogen-Activated Protein Kinases in Ovarian Carcinoma Cells: Inhibition of Extracellular Signal-Regulated Kinase Activity Increases Sensitivity to Cisplatin", *Clin. Cancer Res.*, 1999, pp. 1007-1014, vol. 5.

Rudyi et al. Koordinatsionnaya Khimiya, 1975, p. 1572, vol. 1, XP009041868.

Samatov et al. Izvestiya Akademii Nauk SSSR, Seriya Khimicheskaya, 1974, pp. 2142-2144, XP009041871.

Samatov et al. Izvestiya Akademii Nauk SSSR Seriya Khimicheskaya, 1974, pp. 1467-1472, No. 9, XP009041872.

Sanchez-Perez, I. et al. "Cisplatin Induces a Persistent Activation of JNK That is Related to Cell Death", *Oncogene*, 1998, pp. 533-540, vol. 16.

Schindler, C. et al. "Transcriptional Responses to Polypeptide Ligands: The JAK-STAT Pathway", *Annu. Rev. Biochem.*, 1995, pp. 621-651, vol. 64.

Seidel, H. M. et al. "Spacing of Palindromic Half Sites as a Determinant of Selective STAT (Signal Transducers and Activators of Transcription) DNA Binding and Transcriptional Activity", *Proc. Natl. Acad. Sci. USA*, 1995, pp. 3041-3045, vol. 92.

Smithgall, T. E. et al. "Control of Myeloid Differentiation and Survival by Stats", *Oncogene*, 2000, pp. 2612-2618, vol. 19.

Song, J. I. et al. "STAT Signaling in Head and Neck Cancer", *Oncogene*, 2000, pp. 2489-2495, vol. 19.

Stark, G. R. et al. "How Cells Respond to Interferons", *Annu. Rev. Biochem*, 1998, pp. 227-264, vol. 67.

Toyoizumi, T. et al. "Combined Therapy with Chemotherapeutic Agents and Herpes Simplex Virus Type 1 ICP34.5 Mutant (HSV-1716) in Human Non-Small Cell Lung Cancer", 1999, *Human Gene Therapy*, pp. 3013-3029, vol. 10.

Turkson, J. et al.. "Stat3 Activation by Src Induces Specific Gene Regulation and is Required for Cell Transformation", *Mol. Cell. Biol.*, 1998, pp. 2545-2552, vol. 18, No. 5.

Turkson, J. et al. "Requirement for Ras/Rac1-Mediated p38 and c-Jun N-Terminal Kinase Signaling in Stat3 Transcriptional Activity Induced by the Src Oncoprotein", *Mol. Cell. Biol.*, 1999, pp. 7519-7528, Vol. 19, No. 11.

Turkson, J. et al. "STAT Proteins: Novel Molecular Targets for Cancer Drug Discovery", *Oncogene*, 2000, pp. 6613-6626, vol. 19.

Turkson, J. et al. "Phosphotyrosyl Peptides Block Stat3-Mediated DNA Binding Activity, Gene Regulation, and Cell Transformation", *J. Biol. Chem.*, 2001, pp. 45443-45455, vol. 276, No. 48.

Wagner, B. J. et al. "The SIF Binding Element Confers *sis*/PDGF Inducibility Onto the c-fos Promoter", *EMBO J.*, 1990, pp. 4477-4484, vol. 9, No. 13.

Yu, C. L. et al. "Enhanced DNA-Binding Activity of a Stat3-Related Protein in Cells Transformed by the Src Oncoprotein", *Science*, 1995, pp. 81-83, vol. 269, No. 32.

Zhang, Y. et al. "Activation of Stat3 in v-Src-Transformed Fibroblasts Requires Cooperation of Jak1 Kinase Activity", *J. Biol. Chem.*, 2000, pp. 24935-24944, vol. 275.

Zheligovskaya et al. Vestnik Moskovskogo Universiteta. Khimiya, 1970, pp. 32-37, vol. 11, No. 1, XP009041901.

Chernyaev, I.I. et al. "Nitrosation of amines in platinum (IV) triamines of ribbed structure" *Zhurnal Neorganicheskoi Khimii*, 1967, pp. 1877-1885, vol. 12, No. 7.

Adrianova, O.N. et al. "Anomaly of the acid properties of platinum cis-dinitrotriamines of meridonal structure" *Zhurnal Neorganicheskoi Khimii*, 1978, pp. 2155-2158, vol. 23, No. 8.

Howell, B.A. et al. "Substituted catecholato(1,2-diaminocyclohexane) platinum(II) compounds" *Inorganica Chimica Acta*, 1988, pp. 181-183, vol. 142, No. 2.

Bromberg, J. "Stat proteins and oncogenesis" *J. Clin. Invest.*, 2002, pp. 1139-1142, vol. 109.

Kortepeter, M. G. et al. "Managing Potential Laboratory Exposure to Ebola Virus by Using a Patient Biocontainment Care Unit", *Emerging Infectious Diseases*, Jun. 2008, pp. 881-887, vol. 14, No. 6.

\* cited by examiner

PLATINUM COMPLEXES AND METHODS FOR INHIBITING TUMOR CELL PROLIFERATION

CROSS-REFERENCE TO RELATED APPLICATION

This application is a continuation of U.S. application Ser. No. 11/030,567, filed Jan. 6, 2005, now abandoned which claims the benefit of U.S. Provisional Application Ser. No. 60/534,575, filed Jan. 6, 2004, the disclosure of which is incorporated herein by reference in its entirety, including all tables.

BACKGROUND OF THE INVENTION

Platinum complexes, the prototype of cisplatin, have been widely used as active anticancer agents (Ardizzoni et al., 1999; Nitiss, 2002) in a variety of human tumors, including testicular, ovarian, bladder carcinoma, head and neck, and non-small cell lung cancers. The outcome of treatments with cisplatin and other platinum-containing compounds is strongly linked to their alkylating effects on DNA. However, the potential impact of platinum-complex-based therapy on cellular signaling and the therapeutic importance of such interactions have yet to be explored. Reports show that cisplatin induces activation of members of the mitogen-activated protein kinase (MAPK) pathways (Persons et al., 1999; Sanchez-Perez et al., 1998), which may influence drug-induced apoptosis.

BRIEF SUMMARY OF THE INVENTION

The subject invention concerns platinum complexes and methods for treating disease conditions, such as cancer and tumors, using platinum complexes of the invention.

DETAILED DISCLOSURE OF THE INVENTION

The subject invention concerns platinum complexes and methods for inducing apoptosis and inhibiting tumor cell growth and for treating animals having tumors, cancers, and oncological disease conditions using the subject platinum complexes. Platinum complexes of the subject invention are shown in the Table below:

| Designation | | Structure | $IC_{50}$ |
|---|---|---|---|
| CisPt | | $H_3N$-Pt-$Cl$ / $H_3N$-Pt-$Cl$ | A549: 9.9 ± 4.0<br>Calu-1: 8.6 ± 4.5<br>Panc-1: 4.5 ± 1.9<br>T-24: 1.3 ± 0.4 |
| CPA-1 | | (structure with $NO_2$, Cl, Cl) | A549: 50 ± 23<br>Calu-1: 26 ± 11<br>Panc-1: 19 ± 8.1<br>T-24: 6.2 ± 1.1 |
| CPA-2 | | (structure with $NO_2$, $NO_2$) | A549: >1000<br>Calu-1: 497<br>Panc-1: 890<br>T-24: 560 |
| CPA-3 | | (structure with Cl, Cl) | A549: >250<br>Calu-1: >250<br>Panc-1: 94 ± 65<br>T-24: 23/152/>250 |
| CPA-4 | ("dirty mix") | (structure with $NO_2$, ONO, Cl, ONO) | A549: 50 ± 23<br>Calu-1: 26 ± 11<br>Panc-1: 19 ± 8.1<br>T-24: 6.2 ± 1.1 |
| CPA-4 | ("clean") | same as above | A549: >250<br>Calu-1: >250<br>Panc-1: >250<br>T-24: >250 |
| CPA-5 | | (structure with ONO, ONO, Cl, ONO) | A549: 213<br>Calu-1: 187<br>Panc-1: >250<br>T-24: 111 |
| CPA-6 | | (structure with $NO_2$, ONO, OH, ONO) | |

-continued

| | | | |
|---|---|---|---|
| CPA-7 | | 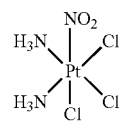 | A549: 20<br>Calu-1: —<br>Panc-1: 6.0<br>T-24: — |
| CPA-8 | | 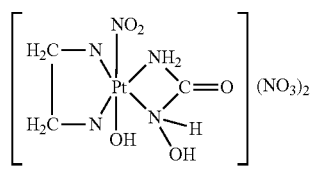 | A549: >250<br>Calu-1: —<br>Panc-1: >250<br>T-24: — |
| CPA-9 | | 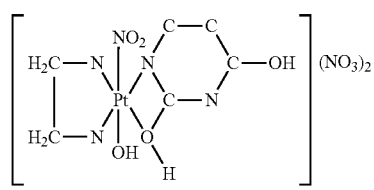 | A549: >250<br>Calu-1: —<br>Panc-1: 6.0<br>T-24: — |
| CPA-10 | | 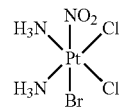 | A549: >250<br>Calu-1: —<br>Panc-1: 6.0<br>T-24: — |
| CPA-11 | | 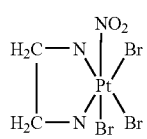 | A549: 138<br>Calu-1: —<br>Panc-1: 48<br>T-24: — |
| CPA-12 | JP1076B<br>cis-[diaminodichloronitro-<br>$C_6H_4O_2$—B—O—$Pt^{IV}$]<br>FW 479.98<br>rec'd May 3, 1999 | 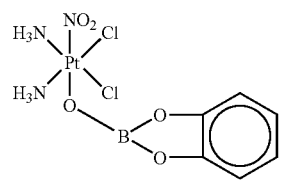 | A549: >250 μM<br>70 μM<br>Calu-1: —<br>Panc-1: >250 μM<br>28 μM<br>T-24: —<br>Panc-1: <1.953 μM<br>2.3 μM<br>4.4 μM<br>2.3 μM |
| CPA-13 | JP1078B<br>$Pt^{IV}$(en)(HOHN—CO—$NH_2$)($NO_2$)5-FU<br>FW 508.39<br>rec'd May 3, 1999 | 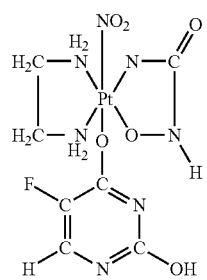 | A549: >250 μM<br>64 μM<br>>250 μM<br>Calu-1: 1.49 μM<br>112 μM |
| CPA-14 | JP1079<br>cis-[$Pt^{IV}$($NH_3$)$_2$$Cl_2$$NO_2$-5FU<br>FW 476.2<br>rec'd Aug. 13, 1999 | 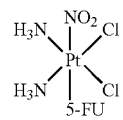 | Panc-1: <1.953 μM<br>1.9 μM<br>2.4 μM<br>10 μM<br>A549: 18 μM<br>4.8 μM<br>38 μM<br>Calu-1: 1.13 μM |
| CPA-15 | JP1080<br>cis-[$Pt^{IV}$($NH_3$)$_2$$Cl_2$$NO_2$-acetate<br>FW 482.2<br>rec'd Aug. 13, 1999 | 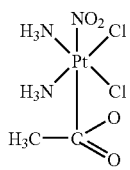 | Panc-1: 3.3 μM<br>17 μM<br>A549: 13.5 μM<br>42 μM |

-continued

| | | | |
|---|---|---|---|
| CPA-16 | JP1082<br>cis-[Pt$^{IV}$(NH$_3$)$_2$Cl$_2$NO$_2$—AsO$_2$<br>FW 453.0<br>rec'd Aug. 13, 1999 | (structure with AsO$_2$) | Panc-1: 4.8 μM<br>20 μM<br>A549: 15 μM<br>39 μM |
| CPA-17 | JP1085A<br>cis-[Pt$^{IV}$(NH$_3$)$_2$Cl$_2$NO$_2$—SeOOH<br>FW 474.1<br>rec'd Aug. 13, 1999 | (structure with SeOOH) | Panc-1: 5.8 μM<br>20 μM<br>A549: 14<br>40 |
| CPA-18 | JP1087A<br>cis-[Pt$^{IV}$(NH$_3$)$_2$Cl$_2$NO$_2$-hydroxyurea<br>FW 422.1<br>rec'd Aug. 13, 1999 | (structure with hydroxyurea) | Panc-1: 5.6 μM<br>3.0 μM<br>4.7 μM<br>A549: 13 μM<br>12 μM<br>Calu-1: 4.2 μM |

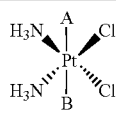

| | Designation | A | B | IC$_{50}$ |
|---|---|---|---|---|
| CPA-19 | JP1081<br>cis-[Pt$^{IV}$(NH$_3$)$_2$Cl$_2$NO$_2$ salicylate]<br>FW 483<br>rec'd Aug. 30, 1999 | —NO$_2$ | salicylate (—O—C(=O)—C$_6$H$_4$—OH) | Panc-1: 20 μM<br>20 μM<br>A549: 37 μM |
| CPA-20 | JP1092A<br>cis-[Pt$^{IV}$(NH$_3$)$_2$Cl$_2$NO$_2$(ONO)]<br>FW 392<br>rec'd Aug. 30, 1999 | —NO$_2$ | —ONO | Panc-1: 15 μM<br>A549: 28 μM |
| CPA-21 | JP1093B<br>cis-[Pt$^{IV}$(NH$_3$)$_2$Cl$_2$NO$_2$Cl<br>FW 382<br>rec'd Aug. 30, 1999 | —NO$_2$ | —Cl | Panc-1: 9.2 μM<br>A549: 4.2 μM |
| CPA-22 | JP1091A<br>cis-[Pt$^{IV}$(NH$_3$)$_2$Cl$_2$NO$_2$(ONO$_2$)<br>FW 408<br>rec'd Aug. 30, 1999 | —NO$_2$ | —ONO$_2$ | Panc-1: 5.4 μM<br>A549: 4.6 μM |
| CPA-23 | JP1089A<br>cis-[Pt$^{IV}$(NH$_3$)$_2$Cl$_2$NO$_2$(H$_2$PO$_4$)<br>FW 443<br>rec'd Aug. 30, 19999 | —NO$_2$ | —OPO$_3$H$_2$ | Panc-1: 3.3 μM<br>5.7 μM<br>1.9 μM<br>A549: 4.2 μM |
| CPA-24 | JP1090A<br>cis-[Pt$^{IV}$(NH$_3$)$_2$Cl$_2$NO$_2$(HSO$_4$)]<br>FW 443<br>rec'd Aug. 30, 1999 | —NO$_2$ | —OSO$_3$H | Panc-1: 5.2 μM<br>9.2 μM<br>5.9 μM<br>A549: 3.8 μM |

| | Desigation | Structure | IC$_{50}$ |
|---|---|---|---|
| CPA-25 | JP0097B<br>cis-[Pt$^{IV}$(NH$_3$)$_2$BrCl$_2$NO$_2$<br>FW 426<br>rec'd Aug. 30, 1999 | (Pt structure with NO$_2$, Br, 2 NH$_3$, 2 Cl) | Panc-1: 5.6 μM<br>13 μM<br>A549: 8.0 μM |
| CPA-26 | 1094C | (Pt complex with o-phenylenediamine, NO$_2$, 2 Cl) | Panc-1: 228 μM |
| CPA-27 | 1084A | ((CH$_3$)$_2$HC—NH and (CH$_3$)$_2$HC—NH ligands, NO$_2$, 2 Cl, F on Pt) | Panc-1: 31 μM<br>35 μM |

-continued

| | | | |
|---|---|---|---|
| CPA-28 | 1083A | [Pt complex: H3N, NO2, Cl, H3N, F, Cl] | Panc-1: 80 µM |
| CPA-29 | 1094B | [Pt complex with phenylenediamine and 2 Cl] | Panc-1: 5.7 µM<br>2.1 µM |
| CPA-30 | Eosin | [Pt(CH3)2(NO2)(Cl)2 complex with eosin] | Panc-1: 5.7 µM<br>4.5 µM |
| CPA-31 | Citrate | [Pt complex with citrate ligand] | Panc-1: 31 µM |
| CPA-32 | Dabco | [Pt complex with DABCO] | Panc-1: 15 µM |
| CPA-33 | Tris | [Pt complex with Tris, (HOCH2)3CNH2] | Panc-1: 10 µM |
| CPA-34 | 1084C | [Pt complex with ethylenediamine and hydroxamate] | |
| CPA-35 | Palmitic | [Pt complex with palmitate, CH3(CH2)14COO] | Panc-1: 7.7 µM<br>21 µM |

-continued
| | | | |
|---|---|---|---|
| CPA-36 | 1,3-diaminopropane | 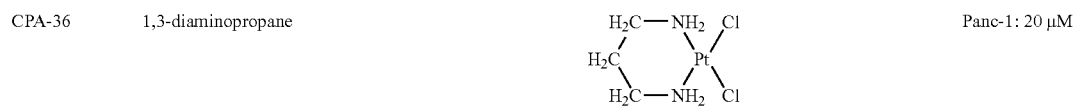 | Panc-1: 20 μM |
| CPA-37 | Hydroxydiaminopropane | 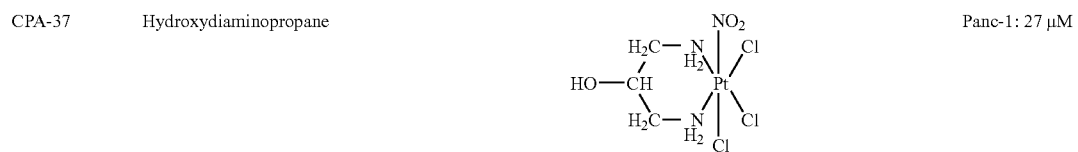 | Panc-1: 27 μM |
| CPA-38 | Histidine | 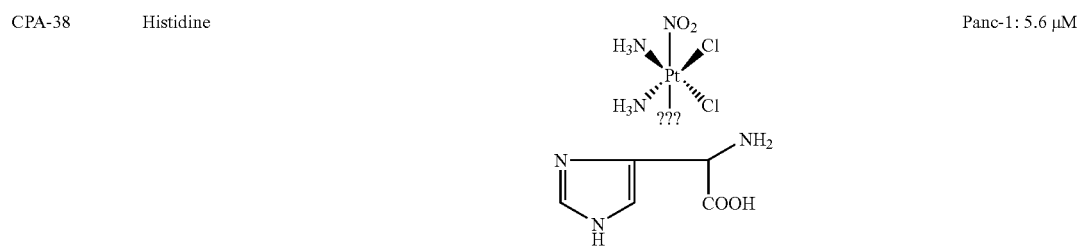 | Panc-1: 5.6 μM |
| CPA-39 | Fluorescein | 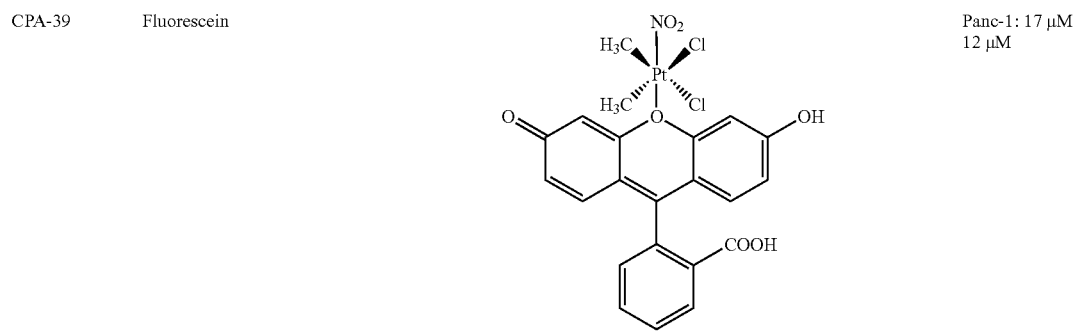 | Panc-1: 17 μM<br>12 μM |
| CPA-40 | 2-aminobutyric acid | 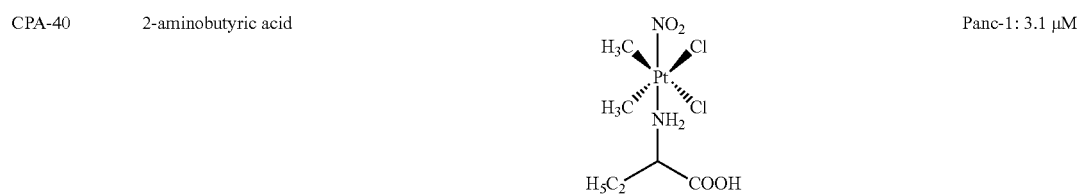 | Panc-1: 3.1 μM |
| CPA-41 | IBF | 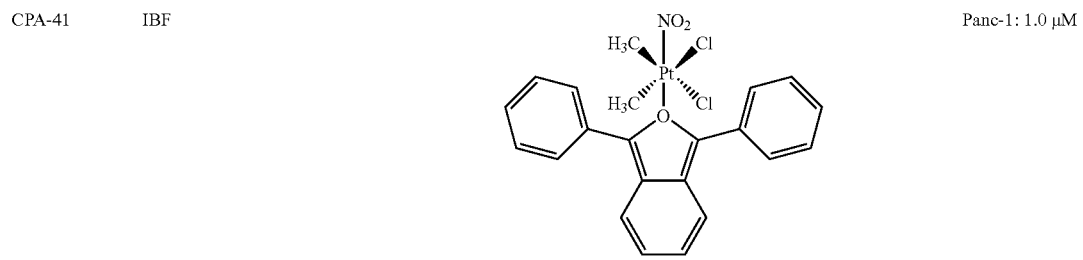 | Panc-1: 1.0 μM |
| CPA-42 | CZ | 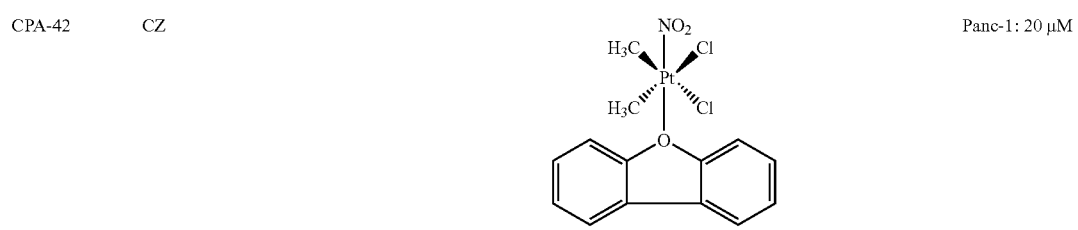 | Panc-1: 20 μM |

-continued
| | | | |
|---|---|---|---|
| CPA-43 | DNP | 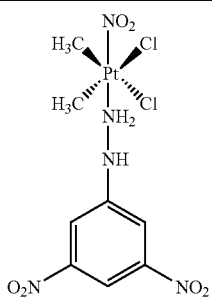 | Panc-1: 3.3 μM<br>4.5 μM |
| CPA-44 | Succinamide | 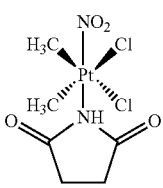 | Panc-1: 6.0 μM |
| CPA-45 | Acridine | 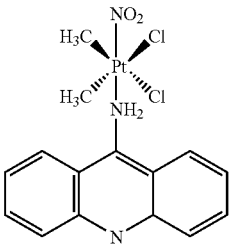 | Panc-1: 3.0 μM |
| CPA-46 | Rhodamine | 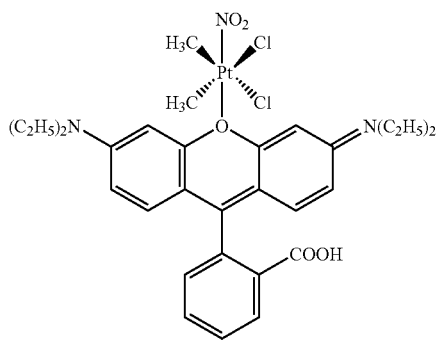 | Panc-1: 3.6 μM<br>4.8 μM |
| CPA-47 | 1094A | 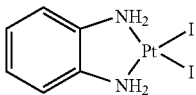 | Panc-1: 3.3 μM |
| CPA-48 | Methyl thymol blue | | Panc-1: 8.6 μM |
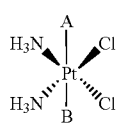
| Designation | | A | IC50 |
|---|---|---|---|
| CPA-49 | D-+-maltose | —NO₂ | Panc-1: 49 μM |
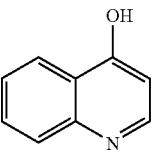

-continued

| | | | | |
|---|---|---|---|---|
| CPA-50 | Morpholine | —NO$_2$ | 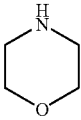 | |
| CPA-51 | 3-aminophthalhydrazide | —NO$_2$ | 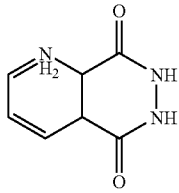 | |
| CPA-52 | Dimethylphthalate | —NO$_2$ | 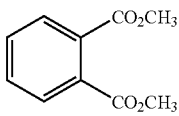 | |
| CPA-53 | 2,7-dichlorofluorescein | —NO$_2$ | 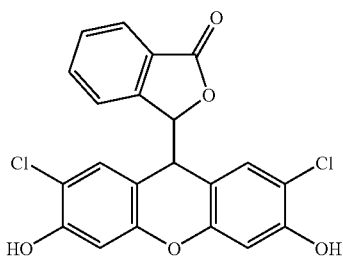 | |
| CPA-54 | 8-hydroxyquinoline | —NO$_2$ | 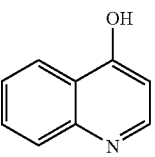 | |
| CPA-55 | Hydrocrotic acid | —NO$_2$ | 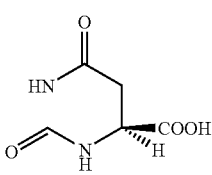 | |
| CPA-56 | Proline | —NO$_2$ | 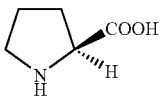 | |
| CPA-57 | Stearic acid | —NO$_2$ | CH$_3$(CH$_2$)$_{16}$COOH | |
| CPA-58 | succinimide | —NO$_2$ | 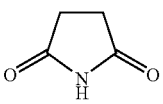 | |

| Designation | | Structure | IC50 |
|---|---|---|---|
| JP3 | [Cis-Pt IV(NH$_3$)$_2$(Cl)$_2$(NO$_2$)(5-FU)] | 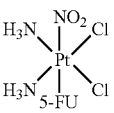 | Panc-1: 2.6 μM |
| JP4 | [Cis-Pt IV(NH$_3$)$_2$(Cl)$_2$(NO$_2$)(n-octanol)] | 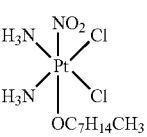 | Panc-1: 18.5 μM |

| | | | |
|---|---|---|---|
| JP5 | [Cis-Pt IV(NH₃)₂(Cl)₂(NO₂)(salicylate)] | 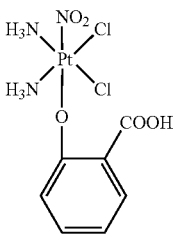 | Panc-1: 6.2 μM |
| JP6 | [Cis-Pt IV(NH₃)₂(Cl)₂(OP(-salicylate)(OH)O)] | 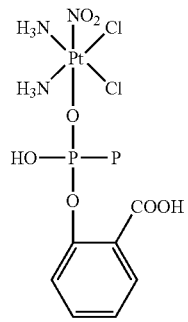 | Panc-1: 5.5 μM |
| GD6 | [Pt IV (1,2-diaminopropane)(Cl)₃(NO₂)] | 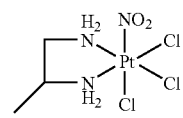 | Panc-1: 9.5 μM |
| GD2 | [cis-diaminonitrosalicylatohydroselenito-Pt IV] | 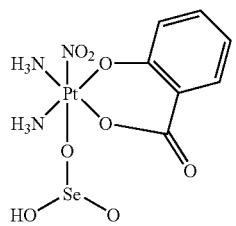 | Panc-1: 60 μM |
| GD3 | [cis-diaminonitrocaticholatohydroselenito-Pt IV] | 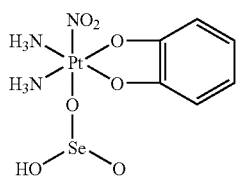 | Panc-1: 49 μM |
| GD4 | [cis-diaminonitrocaticholatoarsenito-Pt IV] | 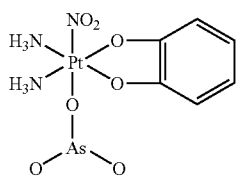 | Panc-1: 73 μM |
| JP13A | [cis-diaminonitrosalicylatoarsenito-Pt IV] | 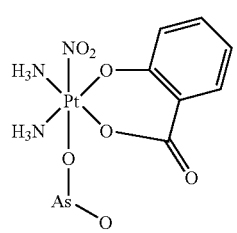 | |

-continued

| | | | |
|---|---|---|---|
| JP14B | [cis-diaminosalicylato-Pt II] | 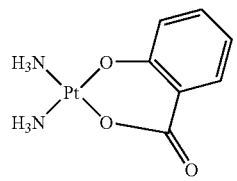 | |
| JP14C | [cis-diaminonitrosalicylato-(5-FU) Pt IV] | 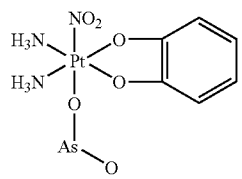 | |
| JP14D | [Cis-diaminonitrosalycilatoarenito- Pt IV] | 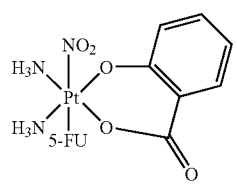 | |
| JP15 | [Cis-diaminonitro-bis(ibuprofen)- Pt IV] | 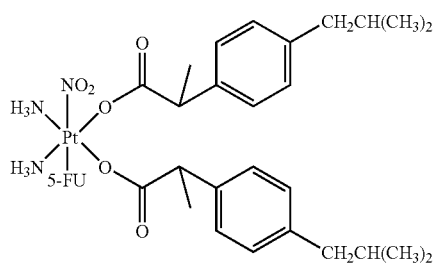 | |
| | 5-FU | | Panc-1: 5.0 μM<br>Calu-1: >250 μM |
| | hydroxyurea | | Panc-1: 1.3 μM<br>Calu-1: >250 μM |
| | Cisplatin | 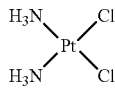 | Panc-1: 1.3 μM<br>Calu-1: 2.0 μM |

Those platinum complexes designated as CPA-19 through CPA-24 and CPA-49 through CPA-58 have the structure:

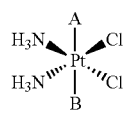

wherein the A and B substituents are as identified in the Table for the particular complex. The substituent can attach to the platinum atom through any suitable atom therein, e.g., a nitrogen, sulfur, or oxygen atom. As used herein, "5FU" means 5-fluorouracil.

The Table shows the results of the various platinum complexes in MTT assays using cell lines A549, Calu-1, Panc-1, and T-24. The IC50 for a particular platinum complex is shown in the far right column of the Table.

Compounds of the subject invention also include pharmaceutically-acceptable salts of the subject platinum complexes. The term pharmaceutically-acceptable salts means salts of the platinum complexes of the invention which are prepared with acids or bases, depending on the particular substituents found on the subject complexes described herein. Examples of a pharmaceutically-acceptable base addition salts include sodium, potassium, calcium, ammonium, or magnesium salt. Examples of pharmaceutically-acceptable acid addition salts include hydrochloric, hydrobromic, nitric, phosphoric, carbonic, sulphuric, and organic acids like acetic, propionic, benzoic, succinic, fumaric, mandelic, oxalic, citric, tartaric, maleic, and the like. Pharmaceutically-acceptable salts of platinum complexes of the invention can be prepared using conventional techniques.

It will be appreciated by those skilled in the art that certain of the platinum complexes of the invention may contain one or more asymmetrically substituted carbon atoms which can give rise to stereoisomers. It is understood that the invention extends to all such stereoisomers, including enantiomers, and diastereoisomers and mixtures, including racemic mixtures thereof.

In one embodiment, methods of the invention comprise inhibiting proliferation of cancerous or tumorigenic cells using the platinum complexes of the present invention.

Platinum complexes of the invention can be delivered to a cell either through direct contact with the cell or via a carrier means. Carrier means for delivering compositions to cells are known in the art and include encapsulating the composition in a liposome moiety, and attaching the platinum complexes to a protein or nucleic acid that is targeted for delivery to the target cell. Published U.S. Patent Application Nos. 20030032594 and 20020120100 disclose amino acid sequences that can be coupled to another composition and that allows the composition to be translocated across biological membranes. Published U.S. Patent Application No. 20020035243 also describes compositions for transporting biological moieties across cell membranes for intracellular delivery.

The subject invention also concerns methods for treating oncological or inflammatory disorders in a patient. In one embodiment, an effective amount of a platinum complex of the present invention is administered to a patient having an oncological or inflammatory disorder and who is in need of treatment thereof. Methods of the invention can optionally include identifying a patient who is or may be in need of treatment of an oncological or inflammatory disorder. The patient can be a human or other mammal, such as a primate (monkey, chimpanzee, ape, etc.), dog, cat, cow, pig, or horse, or other animals having an oncological disorder. Means for administering and formulating platinum complexes for administration to a patient are known in the art, examples of which are described herein. Oncological disorders include cancer and/or tumors of the bone, breast, kidney, mouth, larynx, esophagus, stomach, testis, cervix, head, neck, colon, ovary, lung, bladder, skin, liver, muscle, pancreas, prostate, blood cells (including lymphocytes), and brain. Inflammatory disorders include arthritis, multiple sclerosis, lupus, Crohn's disease, and related neurological and inflammatory connective tissue diseases (e.g., Sjögren's syndrome).

For the treatment of oncological disorders, the platinum complexes of this invention can be administered to a patient in need of treatment in combination with other antitumor or anticancer substances or with radiation therapy or with surgical treatment to remove a tumor. These other substances or radiation treatments may be given at the same as or at different times from the platinum complexes of this invention. For example, the platinum complexes of the present invention can be used in combination with mitotic inhibitors such as taxol or vinblastine, alkylating agents such as cyclophosamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anti-cancer drugs or antibodies, such as, for example, GLEEVEC (imatinib) (Novartis Pharmaceuticals Corporation) and HERCEPTIN (trastuzumab) (Genentech, Inc.), respectively.

Many tumors and cancers have viral genome present in the tumor or cancer cells. For example, Epstein-Barr Virus (EBV) is associated with a number of mammalian malignancies. The platinum complexes of the subject invention can be used alone or in combination with anticancer or antiviral agents, such as ganciclovir, azidothymidine (AZT), lamivudine (3TC), etc., to treat patients infected with a virus that can cause cellular transformation and/or to treat patients having a tumor or cancer that is associated with the presence of viral genome in the cells. The platinum complexes of the subject invention can also be used in combination with viral based treatments of oncologic disease. For example, platinum complexes of the invention can be used with mutant herpes simplex virus in the treatment of non-small cell lung cancer (Toyoizumi et al., 1999).

The subject invention also concerns methods for treating bacterial and viral infections of a patient using a platinum complex of the invention. In one embodiment, an effective amount of a platinum complex of the invention is administered to a patient having a bacterial or viral infection. Methods of the invention can optionally include identifying a patient who is or may be in need of treatment of a bacterial or viral infection. The patient can be a human or other mammal, such as a primate (monkey, chimpanzee, ape, etc.), dog, cat, cow, pig, or horse, or other animal infected with a bacteria or virus. Bacterial infections that can be treated according to the present invention include those from *Staphylococcus, Streptococcus, Salmonella, Bacillus, Clostridium, Pseudomonas, Neisseria, Mycobacterium*, and *Yersinia*. Viral infections that can be treated according to the present invention include, but are not limited to, those associated with human immunodeficiency virus (HIV), human T cell leukemia virus (HTLV), Papillomavirus (e.g, human papilloma virus), Polyomavirus (e.g., SV40, BK virus, DAR virus), orthopoxvirus (e.g., variola major virus (smallpox virus)), EBV, herpes simplex virus (HSV), hepatitis virus, Rhabdovirus (e.g., Ebola virus) and cytomegalovirus (CMV). Platinum compositions of the present invention can also be used to treat viral diseases in the presence of photodynamic therapy (Cuny et al., 1999).

Platinum complexes of the subject invention can also be used to treat patients infected with a parasitic organism. In one embodiment, the patient is administered a therapeutically effective amount of a platinum complex of the present invention. Methods of the invention can optionally include identifying a patient who is or may be in need of treatment of a parasitic infection. The patient can be a human or other mammal, such as a primate (monkey, chimpanzee, ape, etc.), dog, cat, cow, pig, or horse, or other animal infected with a parasitic organism. Disease conditions that can be treated according to the present invention include, but are not limited to, *leishmania*, toxoplasmosis, schistosomiasis, trypanosomiasis, pneumocystis, malaria, and trichinosis. Parasitic organisms that can cause disease conditions treatable according to the present invention include, but are not limited to, *Leishmania, Toxoplasma, Schistosoma, Plasmodium*, and *Trypanosoma*. The subject invention can also be used to treat gastro-intestinal disorders caused by parasitic organisms such as, *Entamoeba, Giardia, Trichomonas*, and nematodes such as *Ascaris, Trichuris, Enterobius, Necator, Ancylostoma, Strongyloides*, and *Trichinella*. In another embodiment, a platinum complex of the present invention can be administered to patients prophylactically, wherein an uninfected patient is traveling to or will be present in an area where parasitic disease is prevalent or poses a risk to the patient. Accordingly, the patient can be treated with a composition of the present invention prior to the patient's exposure to or presence in the area where parasitic disease is prevalent or poses a risk and/or prior to infection with the parasitic organism.

Platinum complexes of the present invention can also be used to treat biological products in vitro that are contaminated with or suspected of being contaminated with a virus on a bacterial or parasitic organism. Biological products which can be treated with a platinum complexes of the present invention include, but are not limited to, whole blood, fractionated blood, plasma, serum, whole organs, or parts of organs, and cells, including blood cells, muscle cells, skin cells, and neural cells, and products derived from cells. Products derived from cells which can be treated with a platinum complex of the present invention include, but are not limited to, interferons, interleukins, blood clotting factors such as factor VIII, IX, X, and the like, insulin, polyclonal and monoclonal antibodies, growth factors, cytokines, and other products. Treatment of biological products comprises contacting the product for an effective amount of time and with an effective amount of a platinum complex of the present invention. If necessary, the biological product can be subsequently washed, preferably with a suitable sterile wash solution such as phosphate buffered saline, to remove the platinum complex that was used to treat the product.

Therapeutic application of the subject platinum complexes, and compositions containing them, can be accomplished by any suitable therapeutic method and technique presently or prospectively known to those skilled in the art. The subject platinum complexes can be administered by any suitable route known in the art including, for example, oral, nasal, rectal, and parenteral routes of administration. As used herein, the term parenteral includes subcutaneous, intravenous, intramuscular, and intrasternal administration, such as by injection. Administration of the subject platinum complexes of the invention can be continuous or at distinct intervals as can be readily determined by a person skilled in the art.

Compounds useful in the methods of the subject invention can be formulated according to known methods for preparing pharmaceutically useful compositions. Formulations are described in detail in a number of sources which are well known and readily available to those skilled in the art. For example, *Remington's Pharmaceutical Science* by E. W. Martin describes formulations which can be used in connection with the subject invention. In general, the compositions of the subject invention will be formulated such that an effective amount of the bioactive platinum complex is combined with a suitable carrier in order to facilitate effective administration of the composition. The compositions used in the present methods can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically acceptable carriers and diluents which are known to those skilled in the art. Examples of carriers or diluents for use with the subject platinum complexes include ethanol, dimethyl sulfoxide, glycerol, alumina, starch, and equivalent carriers and diluents. To provide for the administration of such dosages for the desired therapeutic treatment, new pharmaceutical compositions of the invention will advantageously comprise between about 0.1% and 99%, and especially, 1 and 15% by weight of the total of one or more of the subject platinum complexes based on the weight of the total composition including carrier or diluent.

The compounds of the subject invention can also be administered utilizing liposome technology, slow release capsules, implantable pumps, and biodegradable containers. These delivery methods can, advantageously, provide a uniform dosage over an extended period of time. The platinum complexes of the present invention can also be administered in their salt derivative forms or crystalline forms known to those of ordinary skill in the art.

The subject invention also concerns a packaged dosage formulation comprising in one or more containers at least one platinum compound of the subject invention formulated in a pharmaceutically acceptable dosage.

All patents, patent applications, provisional applications, and publications referred to or cited herein are incorporated by reference in their entirety, including all figures and tables, to the extent they are not inconsistent with the explicit teachings of this specification.

Materials and Methods

Synthesis of NitroPlatinum (IV) Complexes.

Cis-diammineoplatinum(II) dichloride (cisplatin) can be purchased at 99.9% purity from Sigma-Aldrich (#P4394). Using 0.300 grams of Cisplatin (0.00100 moles, FW=300.1), 150 mL of ultra deionized water and 50 mL of dichloroethane are added to a 250-mL Erlenmeyer flask. However, hexane or any organic solvents can be substituted in place of the dichlorethane used here. The choice of a sixth ligand includes the availability of a nitrogen, sulfur or oxygen atom in the chemical structure providing a Lewis base for bonding to the oxidized Pt. Other bondings are possible with metals, halides (such as HCl) or through chelation or interaction with pi molecular orbitals. One mole of the chosen ligand per mole of cisplatin should be weighed and added to the mixture. Organic solvents, such as dichloroethane, provide solubility for organic ligands of hydrophobic nature. A magnetic stir bar is placed in the mixture and the flask placed on a magnetic stir plate in a chemical fume hood. A lecture bottle of dinitrogen tetroxide is fitted with a regulator and Teflon hose, with a glass pipet attached to the hose outlet. The pipet tip is inserted into the lower solvent (e.g., dichloroethane) and the lecture bottle warmed slightly with a warm water bath. Nitrogen dioxide gas is released at a rate of approximately one bubble per second into the stirring mixture. The gas should be added until all the yellow cisplatin is consumed; the disappearance of yellow solids and yellow solution will indicate consumption of the available cisplatin. A blue color is noted to indicate formation of the nitrosyl intermediate; variations in hue and duration of this color have been observed. Gas addition is then terminated (remove the pipet to prevent vacuum suction into the lecture bottle) and the flask covered in aluminum foil to prevent light exposure. The flask should be left to stir overnight, uncovered.

Additional nitrogen dioxide may be added the next day to check for completeness of reaction. A blue color would indicate incomplete oxidation of platinum (II). Normally, this blue fades within ten minutes. For a colorless ligand, the solution has become yellow overnight. If blue color remains, allow it to continue stirring. The mixture requires air for complete oxidation, so should not be tightly covered. Continued oxidation with air can be accelerated using air blown through a trap into the Erlenmeyer, over the liquids. The solvents will evaporate in about two days, leaving a yellow precipitate, which is the product.

The precipitate can be purified via recrystallization in methanol, DMSO, or other suitable solvent. Alternatively, the product can be purified on silica columns or using HPLC.

MTT Assay.

Inhibition of the growth of human tumor cells was carried out in 96-well plates using the MTT assay Cells were plated and treated with various concentrations of the platinum complex for 4 days. Cell viability then was determined by adding to the cells 1 mg/ml media of 3-(4-5-dimethyl-thiazol-2-yl)-2,5-diphenyl tetrazolium bromide (MTT), and incubating the cells for 3 hrs at 37° C. The dye-containing media was replaced by DMSO. After a 5 min incubation with DMSO, absorbance of the control compared to inhibitor treated columns of the 96-well plate was then read at 540 nM with a microtiter plate reader and IC50s determined.

XTT Assay.

A 96-well plate was used for the assays. Approximately $2.5 \times 10^4$ cells in log phase were added to each well. A platinum complex of the invention was dispensed into each well (dissolved in 20% DMSO and 80% media), with additional media added as needed to account for uniform volumes. Control wells contained only cells and media. Each concentration assay was performed in triplicate. Plates were incubated for 48 hours at 37° C. with 7.5% CO2. XTT from MD Biosciences, Quebec, was then added according to the provided protocol concentrations and allowed to react for 3 hours. Plates were agitated 5 minutes before reading absorbance at 475 nm on a Varian Cary 50 spectrophotometer with a fibre-optic probe. Percent survival as compared to control wells was plotted against platinum complex concentration.

It should be understood that the examples and embodiments described herein are for illustrative purposes only and that various modifications or changes in light thereof will be suggested to persons skilled in the art and are to be included within the spirit and purview of this application and the scope of the appended claims.

REFERENCES

Published U.S. Patent Application No. 20030032594
Published U.S. Patent Application No. 20020120100
Published U.S. Patent Application No. 20020035243
Ardizzoni, A., Antonelli, G., Grossi, F., Tixi, L., Cafferata, M., Rosso, R. (1999) "The combination of etoposide and cisplatin in non-small-cell lung cancer (NSCLC)" *Ann. Oncol.* 10:S13-17.
Cuny, G. D. et al. (1999) "Photoactivated virucidal properties of tridentate 2,2'-dihydroxyazobenzene and 2-salicylideneaminophenol platinum pyridine complexes" *Bioorganic and Medicinal Chemistry Letters* 9(2):237-240.
Nitiss, J. L. (2002) "A copper connection to the uptake of platinum anticancer drugs" *Proc. Natl. Acad. Sci. USA* 99:13963-13965.
Persons, D. L., Yazlovitskaya, E. M., Cui, W., Pelling, J. C. (1999) "Cisplatin-induced Activation of Mitogen-activated Protein Kinases in Ovarian Carcinoma Cells: Inhibition of Extracellular Signal-regulated Kinase Activity Increases Sensitivity to Cisplatin" *Clin. Cancer Res.* 5:1007-1014.
Sanchez-Perez, I., Murguia, J. R., Perona, R. (1998) "Cisplatin induces a persistent activation of JNK that is related to cell death" *Oncogene* 16:533-540.
Toyoizumi, T., R. Mick, A. E. Abbas, E. H. Kang, L. R. Kaiser, K. L. Molnar-Kimber (1999) "Combined therapy with chemotherapeutic agents and herpes simplex virus type IICP34.5 mutant (HSV-1716) in human non-small cell lung cancer" *Human Gene Therapy* 10(18):17.

We claim:
1. A method for treating an oncological disorder in a patient, said method comprising administering an effective amount of a platinum complex to the patient, wherein said platinum complex has the structure:

CPA-2
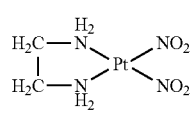

CPA-5
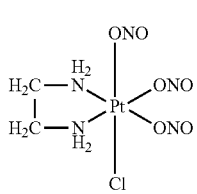

CPA-6
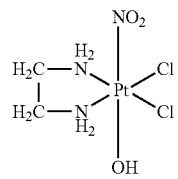

CPA-8
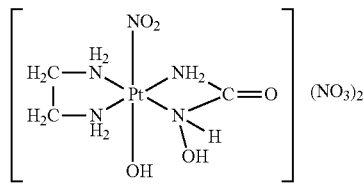

CPA-9
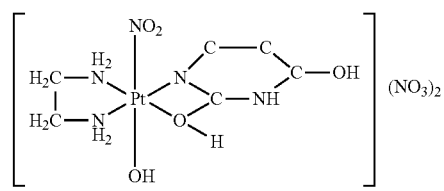

CPA-10
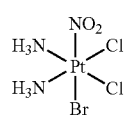

CPA-12
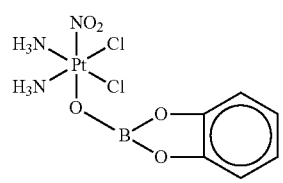

CPA-13
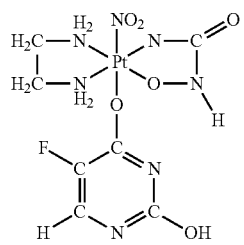

CPA-14
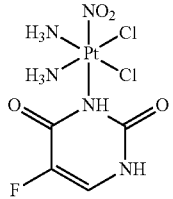

CPA-15
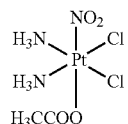

CPA-16
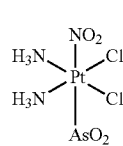

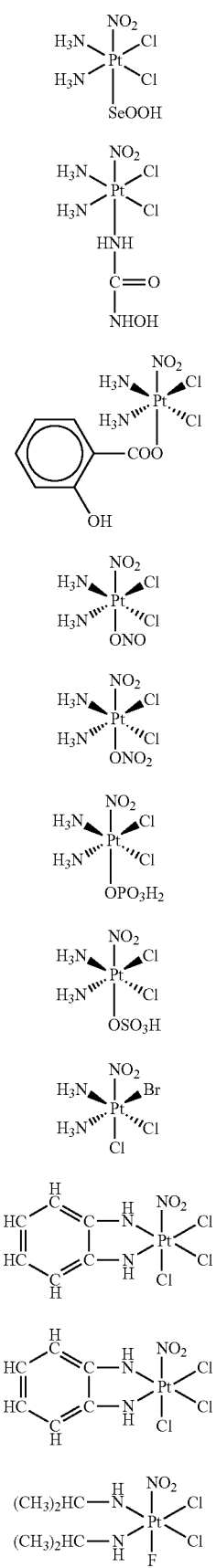
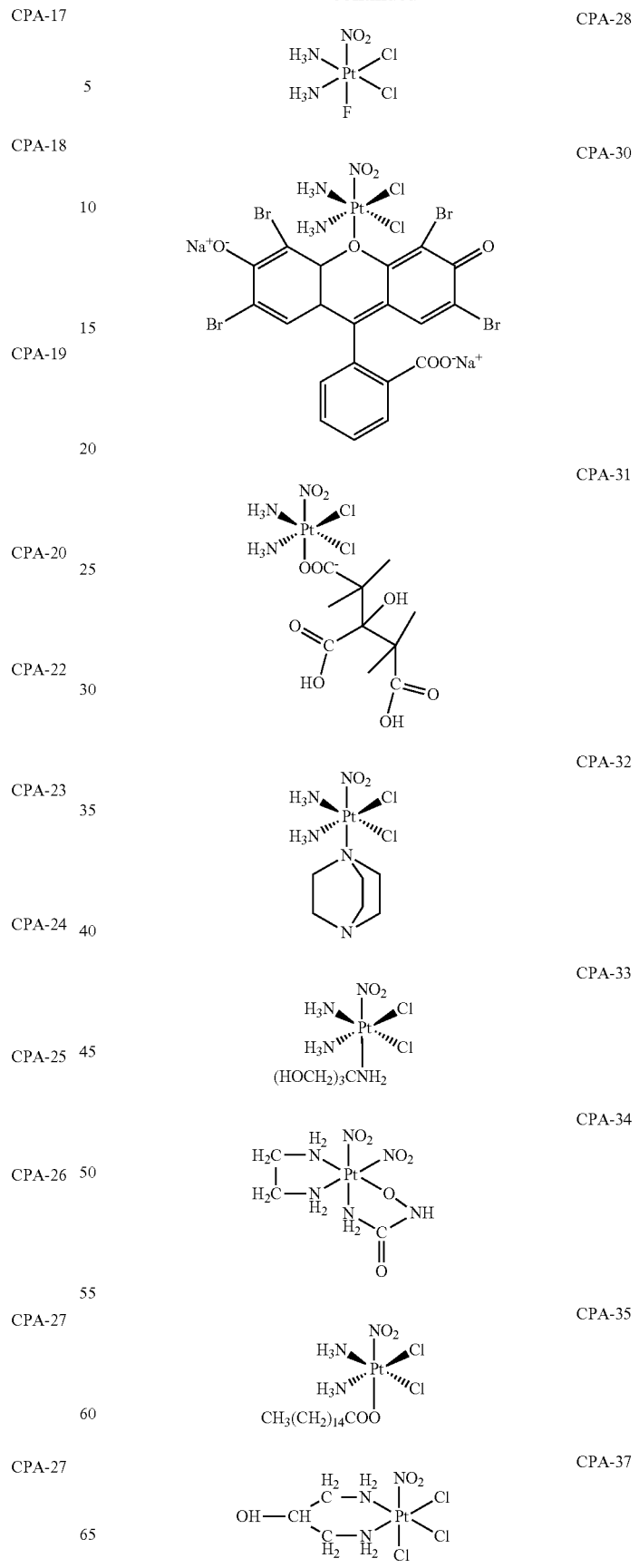

27
-continued
CPA-38
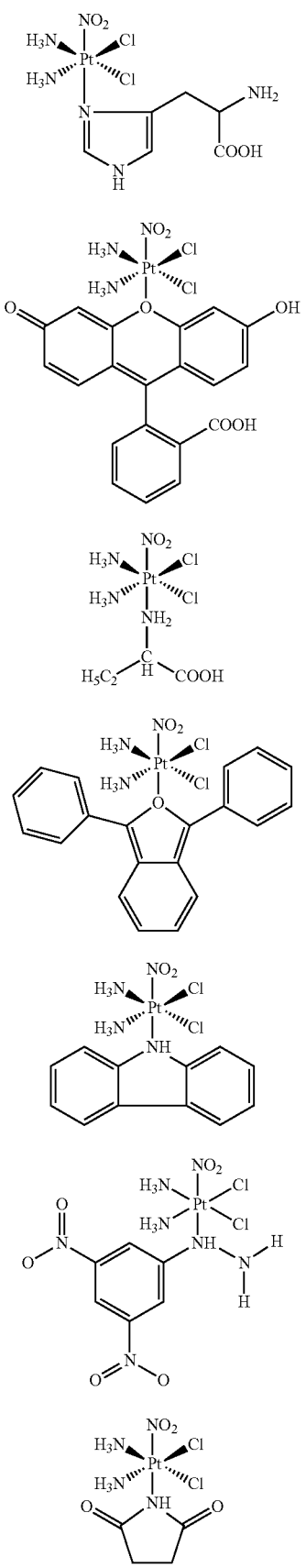
CPA-39
CPA-40
CPA-41
CPA-42
CPA-43
CPA-44
28
-continued
CPA-45
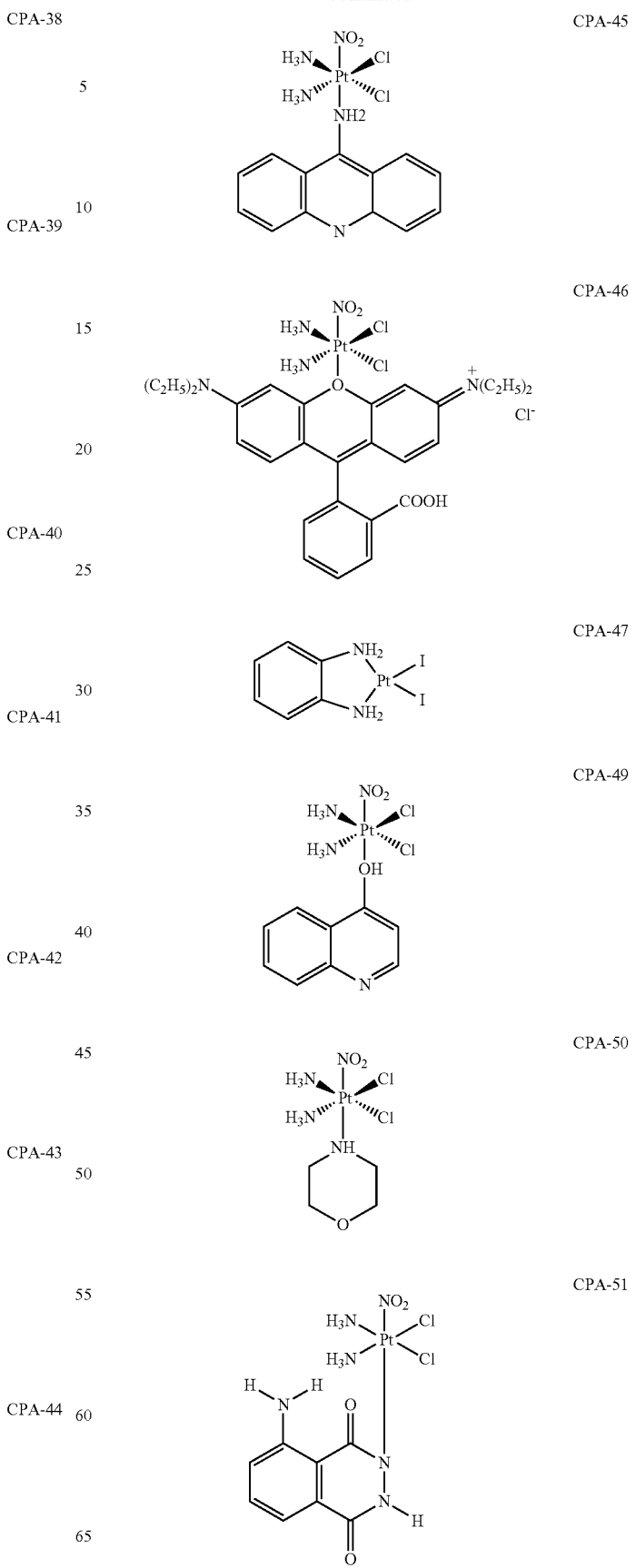
CPA-46
CPA-47
CPA-49
CPA-50
CPA-51

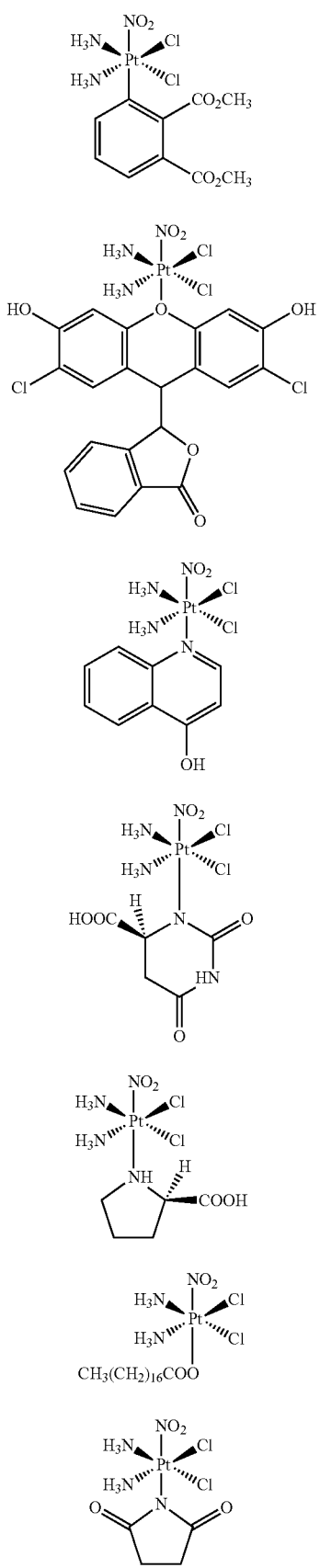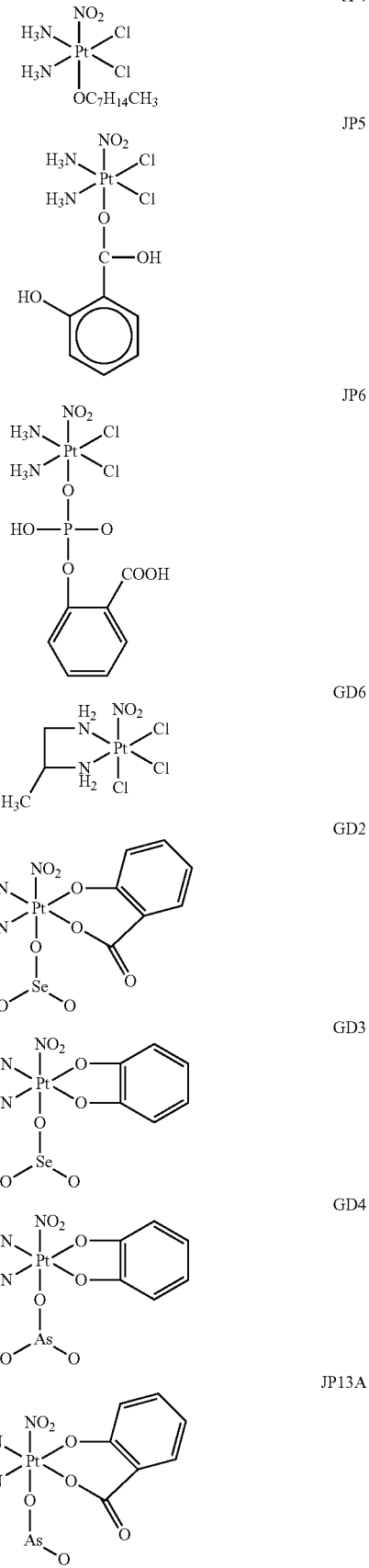

-continued

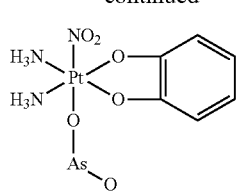
JP14C

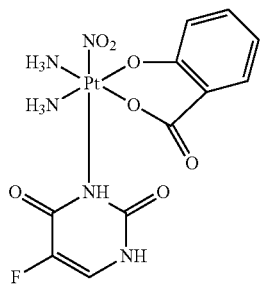
JP14D or

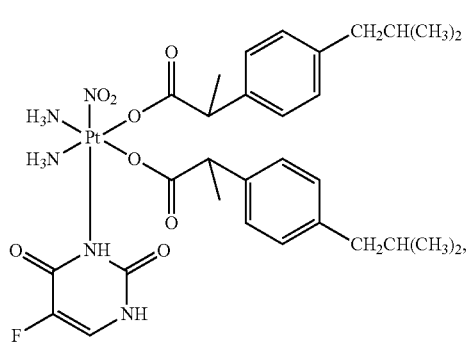
JP15 or a pharmaceutically acceptable salt of any of the foregoing; and wherein said oncological disorder is ovarian cancer, testicular cancer, bladder cancer, pancreatic cancer, or lung cancer.

2. The method according to claim 1, wherein the patient is a mammal.

3. The method according to claim 1, wherein the patient is a human, monkey, chimpanzee, ape, dog, cat, horse, cow, or pig.

4. The method according to claim 1, wherein said platinum complex is encapsulated in a liposome moiety or said platinum complex comprises a protein or nucleic acid that targets delivery of the platinum complex to a cell or said platinum complex comprises a moiety for transport across a cell membrane for intracellular delivery.

5. The method according to claim 1, wherein said platinum complex is administered to the patient via an oral, nasal, rectal, or parenteral route.

6. The method according to claim 1, wherein said platinum complex is administered in combination with other antitumor or anticancer substances or is administered in combination with radiation therapy or surgical treatment.

7. The method according to claim 6, wherein said substance is a mitotic inhibitor, an alkylating agent, an antimetabolite, a DNA intercalator, a topoisomerase inhibitor, an antiangiogenic agent, an antiestrogen, or an anti-cancer antibody.

8. The method according to claim 6, wherein said antitumor or anticancer substances, therapy, or treatment are provided at times different from administration of said platinum complex.

9. The method according to claim 1, wherein said platinum complex is provided in a pharmaceutically acceptable composition.

10. The method according to claim 1, wherein said method comprises identifying a patient who is or may be in need of treatment of said disorder.

11. A method for inhibiting the proliferation of a cancerous or tumorigenic cell, said method comprising contacting said cell with an effective amount of a platinum complex, wherein said platinum complex has the structure:

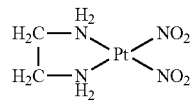
CPA-2

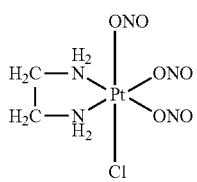
CPA-5

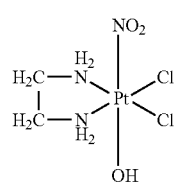
CPA-6

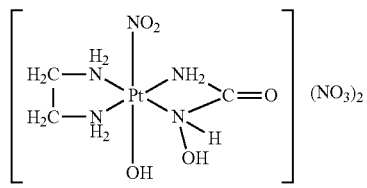
CPA-8

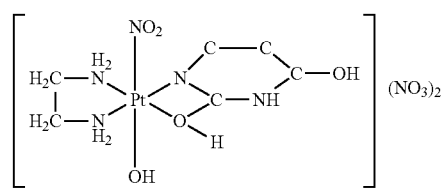
CPA-9

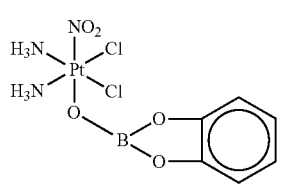
CPA-10

CPA-12

CPA-13
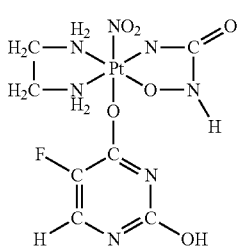
CPA-14
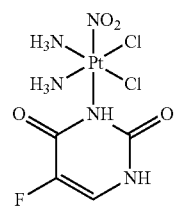
CPA-15
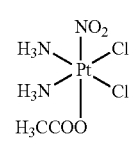
CPA-16
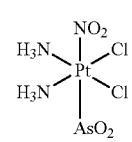
CPA-17
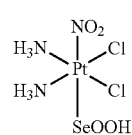
CPA-18
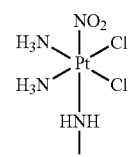
CPA-19
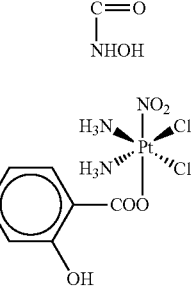
CPA-20
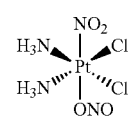
CPA-22
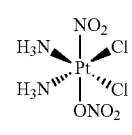
CPA-23
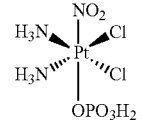
CPA-24
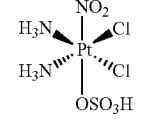
CPA-25
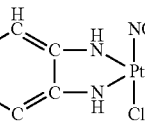
CPA-26
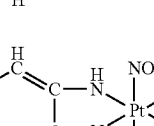
CPA-27
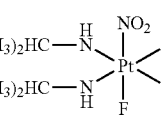
CPA-27
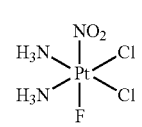
CPA-28
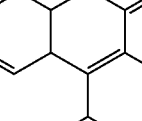
CPA-30
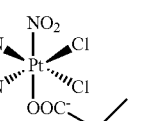
CPA-31
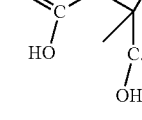

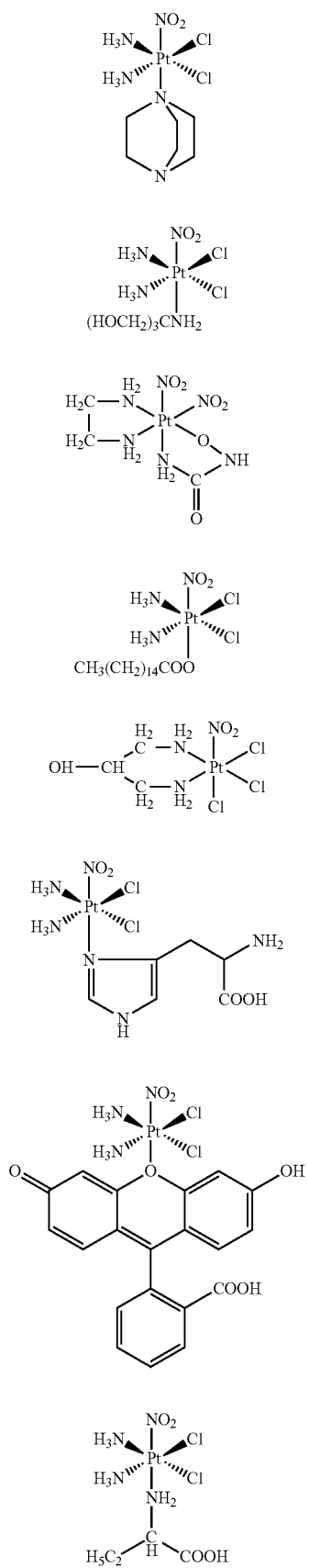
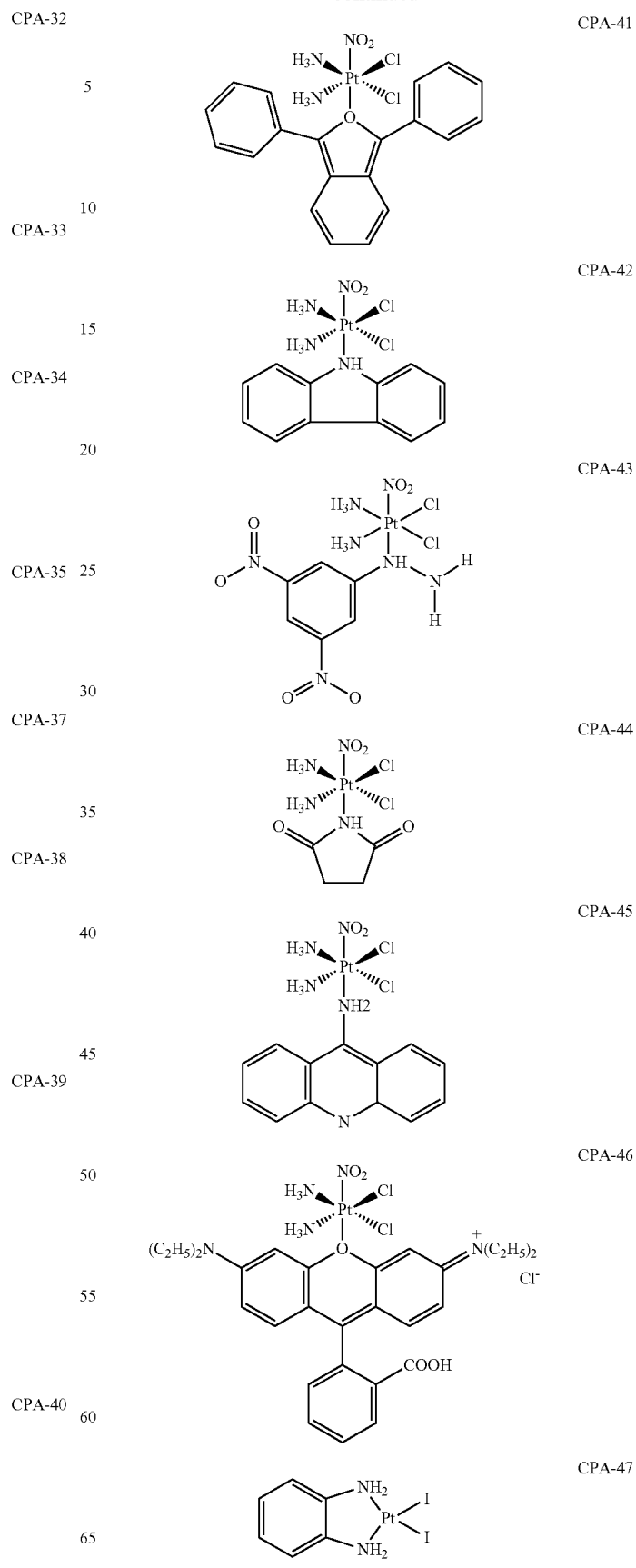

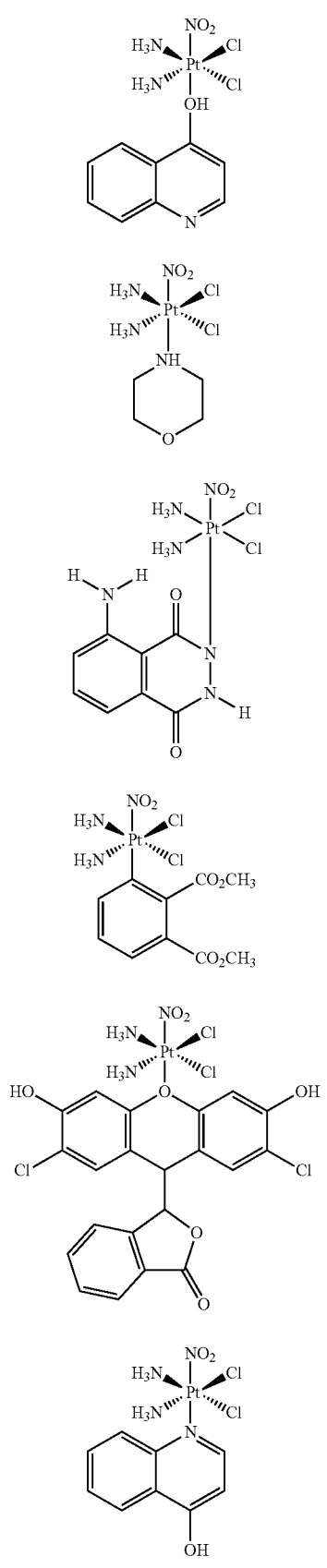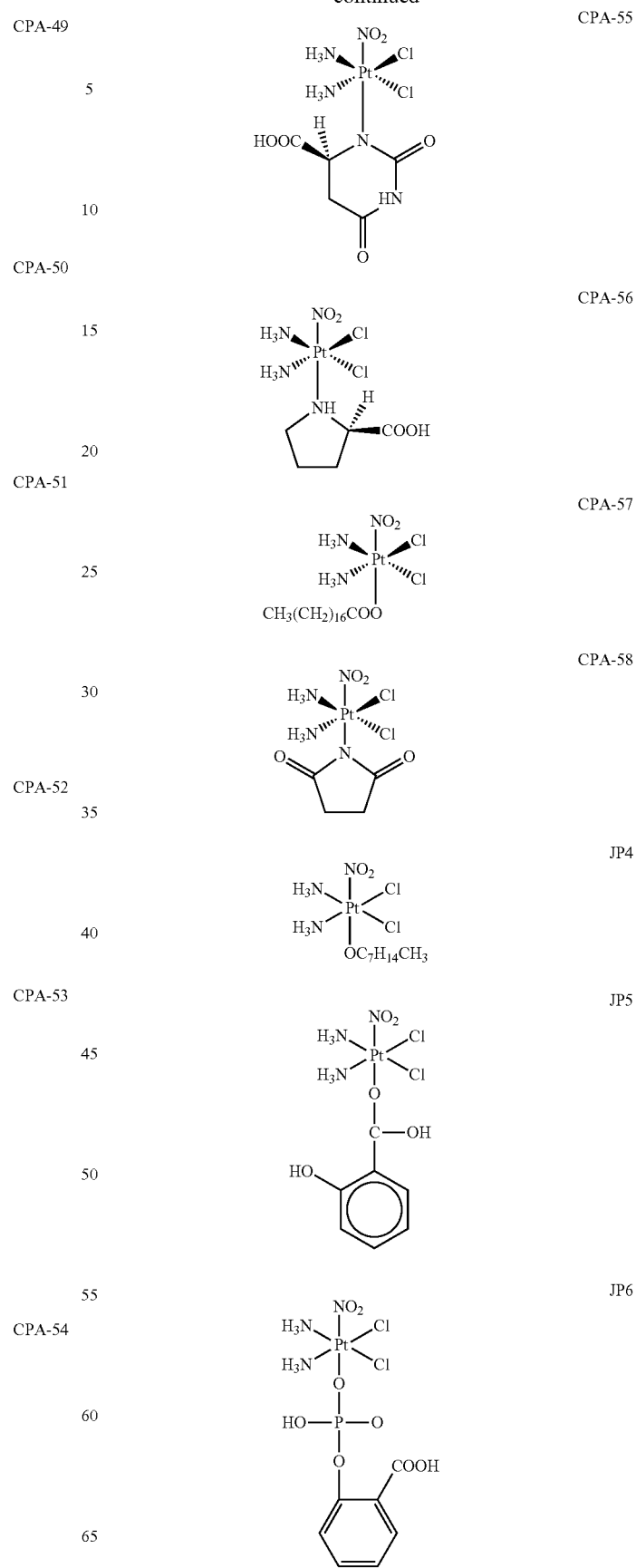

-continued

GD6 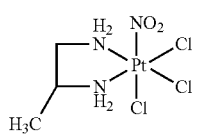

GD2 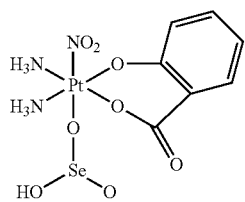

GD3 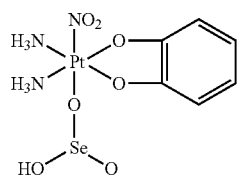

GD4 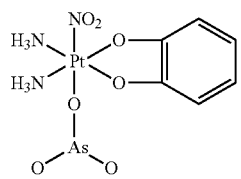

JP13A 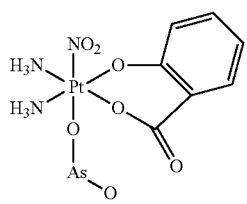

JP14C 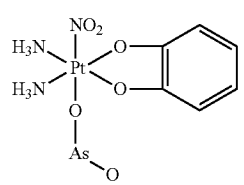

JP14D 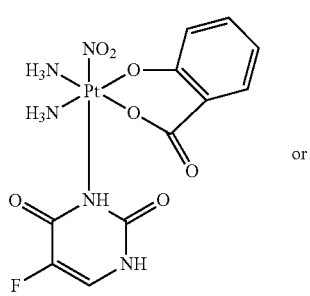 or

-continued

JP15 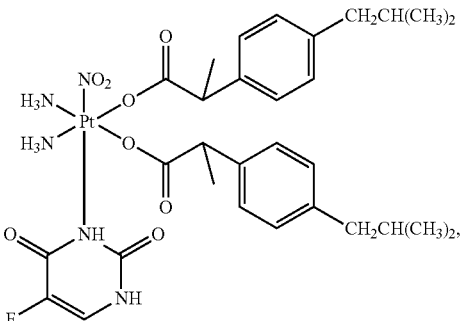

or a pharmaceutically acceptable salt of any of the foregoing; and wherein said cell is an ovarian cell, a testicular cell, a bladder cell, a pancreatic cell, or a lung cell.

12. The method according to claim 11, wherein the cell is a mammalian cell.

13. The method according to claim 11, wherein the cell is from a human, monkey, chimpanzee, ape, dog, cat, horse, cow, or pig.

14. The method according to claim 11, wherein said platinum complex is encapsulated in a liposome moiety or said platinum complex comprises a protein or nucleic acid that targets delivery of the platinum complex to the cell.

15. The method according to claim 6, wherein said antitumor or anticancer substance is taxol, vinblastine, cyclophosamide, ifosfamide, 5-fluorouracil, hydroxyurea, adriamycin, bleomycin, etoposide, camptothecin, angiostatin, tamoxifen, imatinib, or trastuzumab.

16. The method according to claim 1, wherein said platinum complex is administered to said patient in a liposome, a slow release capsule, an implantable pump, or a biodegradable container.

17. The method according to claim 1, wherein said pharmaceutically acceptable salt is a sodium salt, potassium salt, calcium salt, ammonium salt, magnesium salt, hydrochloric salt, hydrobromic salt, nitric salt, phosphoric salt, carbonic salt, sulphuric salt, acetic salt, propionic salt, benzoic salt, succinic salt, fumaric salt, mandelic salt, oxalic salt, citric salt, tartaric salt, or maleic salt.

18. The method according to claim 11, wherein said pharmaceutically acceptable salt is a sodium salt, potassium salt, calcium salt, ammonium salt, magnesium salt, hydrochloric salt, hydrobromic salt, nitric salt, phosphoric salt, carbonic salt, sulphuric salt, acetic salt, propionic salt, benzoic salt, succinic salt, fumaric salt, mandelic salt, oxalic salt, citric salt, tartaric salt, or maleic salt.

19. The method according to claim 1, wherein the patient is a human.

20. The method according to claim 11, where said platinum complex is provided with a carrier.

* * * * *

UNITED STATES PATENT AND TRADEMARK OFFICE
CERTIFICATE OF CORRECTION

PATENT NO. : 7,977,381 B2
APPLICATION NO. : 11/703497
DATED : July 12, 2011
INVENTOR(S) : Heidi Kay et al.

It is certified that error appears in the above-identified patent and that said Letters Patent is hereby corrected as shown below:

Column 2,
Structure corresponding to CPA-6,

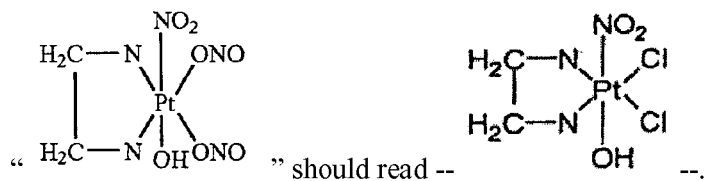

Column 6,
Line 3 in corresponding to $IC_{50}$ column of CPA-17, "A549: 14" should read --A549: 14µM--.
Line 4 in corresponding $IC_{50}$ column of CPA-17, "40" should read --40µM--.

Columns 7 and 8,
Structure corresponding to CPA-30,

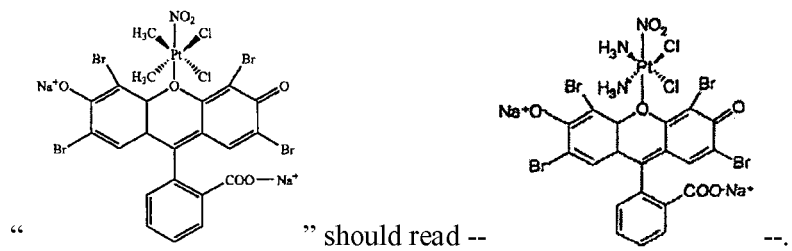

Signed and Sealed this
Seventeenth Day of April, 2012

David J. Kappos
*Director of the United States Patent and Trademark Office*

Columns 7 and 8,
Structure corresponding to CPA-34,
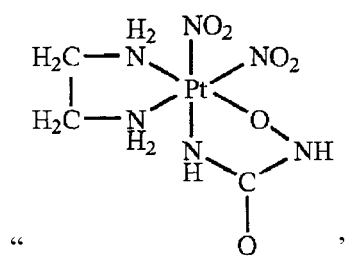 " should read -- 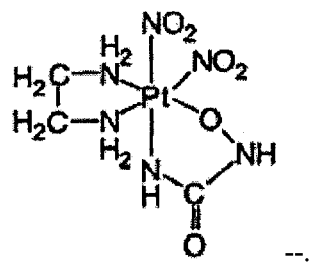 --.
Columns 9 and 10,
Structure corresponding to CPA-39,
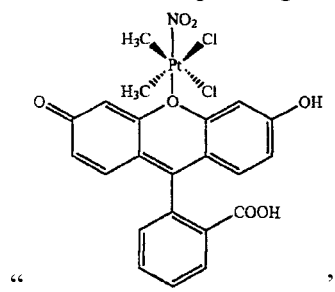 " should read -- 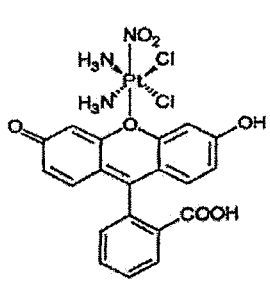 --.
Columns 9 and 10,
Structure corresponding to CPA-40,
" 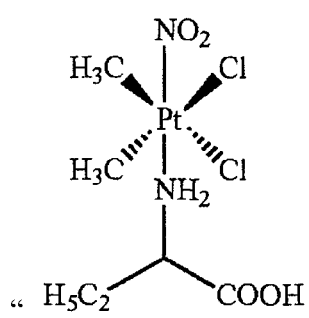 " should read -- 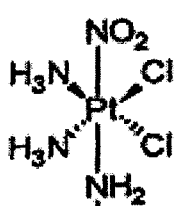 --.
Structure corresponding to CPA-41,
" 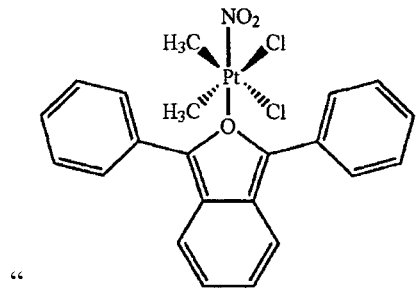 " should read -- 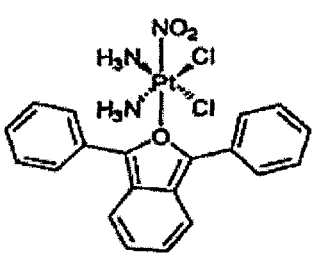 --.

CERTIFICATE OF CORRECTION (continued)
U.S. Pat. No. 7,977,381 B2

Columns 9 and 10,
Structure corresponding to CPA-42,

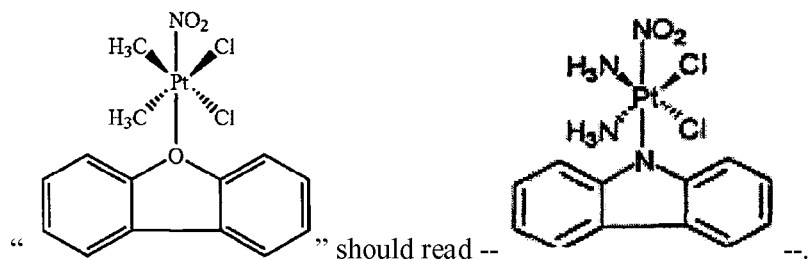 should read -- --.

Columns 11 and 12,
Structure corresponding to CPA-43,

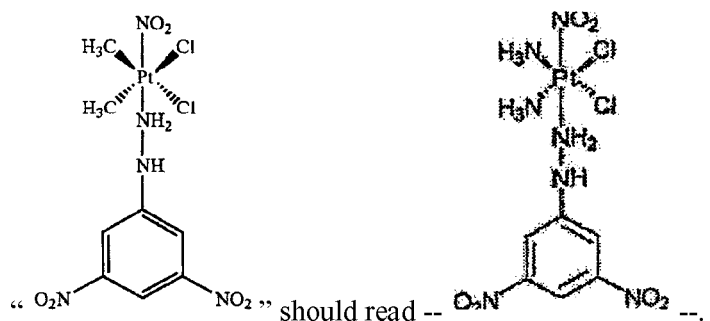 should read -- --.

Columns 11 and 12,
Structure corresponding to CPA-46,

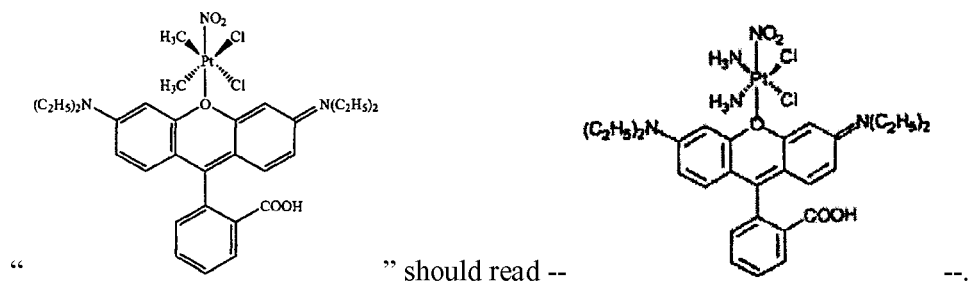 should read -- --.

Column 13,
Designation for CPA-55, "Hydrocrotic acid" should read --Hydroorotic acid--.

Columns 15 and 16,
Structure corresponding to JP6,

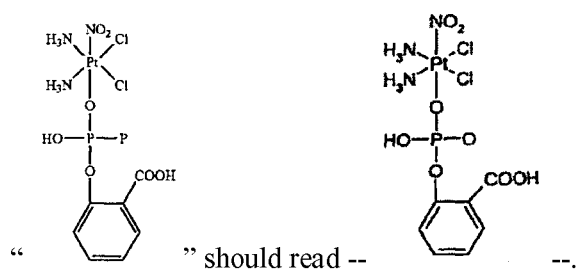 should read -- --.

CERTIFICATE OF CORRECTION (continued)
U.S. Pat. No. 7,977,381 B2

Column 25,
Structures corresponding to CPA-26 and CPA-27,

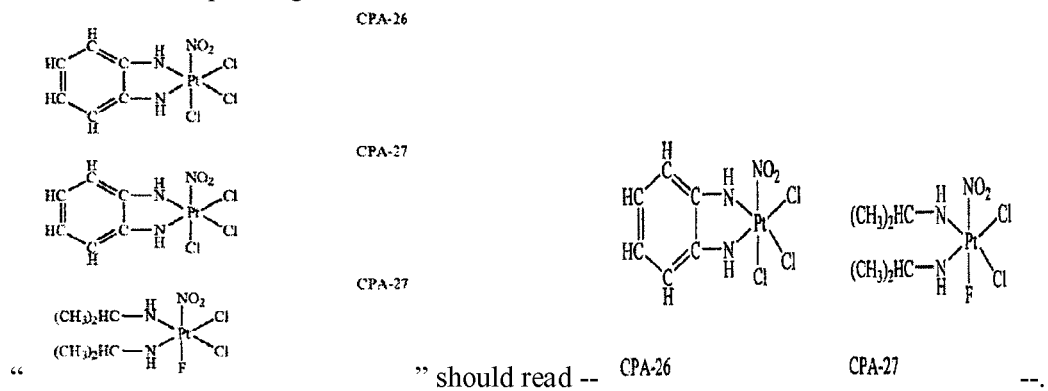

" should read --

Column 34,
Structures corresponding to CPA-26 and CPA-27,

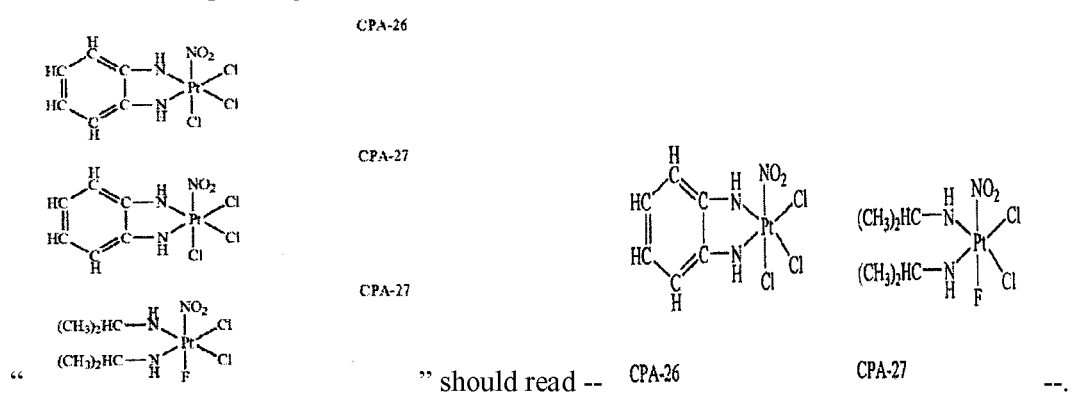

" should read --

UNITED STATES PATENT AND TRADEMARK OFFICE
CERTIFICATE OF CORRECTION

PATENT NO. : 7,977,381 B2
APPLICATION NO. : 11/703497
DATED : July 12, 2011
INVENTOR(S) : Heidi Kay et al.

Page 1 of 5

It is certified that error appears in the above-identified patent and that said Letters Patent is hereby corrected as shown below:

Column 2,
Structure corresponding to CPA-6,

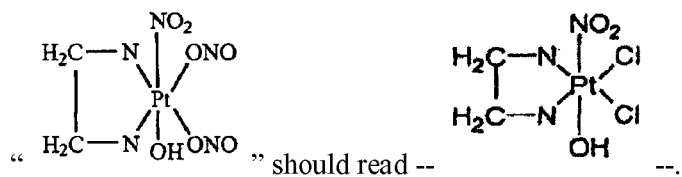 should read -- --.

Column 6,
Line 3 in corresponding to $IC_{50}$ column of CPA-17, "A549: 14" should read --A549: 14μM--.
Line 4 in corresponding $IC_{50}$ column of CPA-17, "40" should read --40μM--.

Columns 7 and 8,
Structure corresponding to CPA-30,

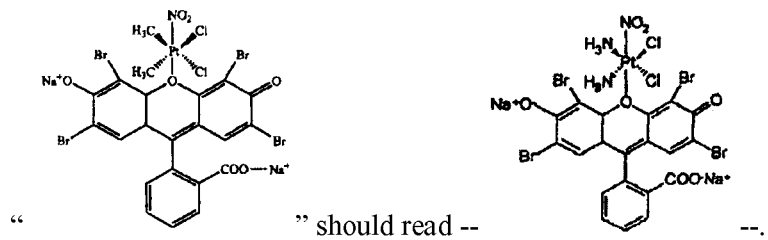 should read -- --.

This certificate supersedes the Certificate of Correction issued April 17, 2012.

Signed and Sealed this
Nineteenth Day of June, 2012

David J. Kappos
*Director of the United States Patent and Trademark Office*

Columns 7 and 8,
Structure corresponding to CPA-34,
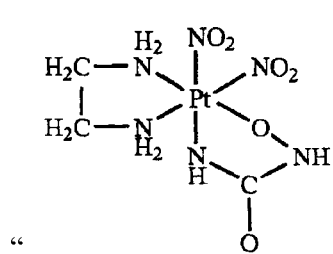 " should read -- 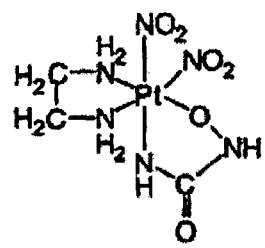 --.
Columns 9 and 10,
Structure corresponding to CPA-39,
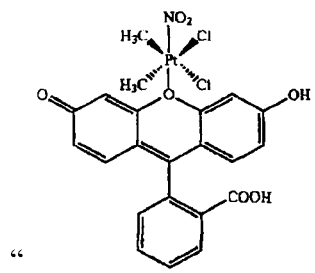 " should read -- 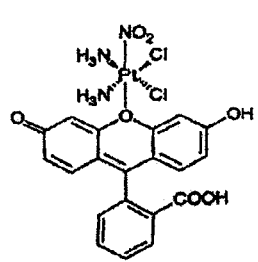 --.
Columns 9 and 10,
Structure corresponding to CPA-40,
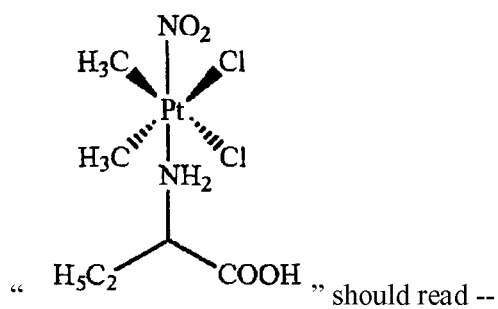 " should read -- 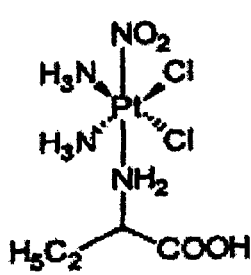 --.
Structure corresponding to CPA-41,
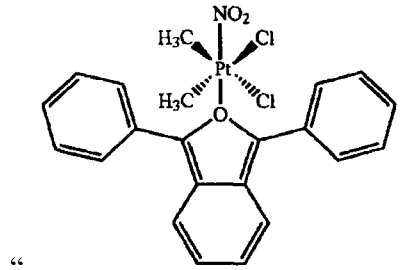 " should read -- 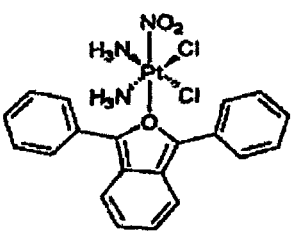 --.

CERTIFICATE OF CORRECTION (continued)
U.S. Pat. No. 7,977,381 B2

Columns 9 and 10,
Structure corresponding to CPA-42,

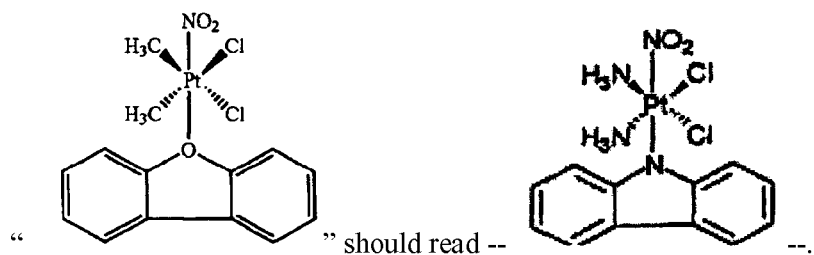

Columns 11 and 12,
Structure corresponding to CPA-43,

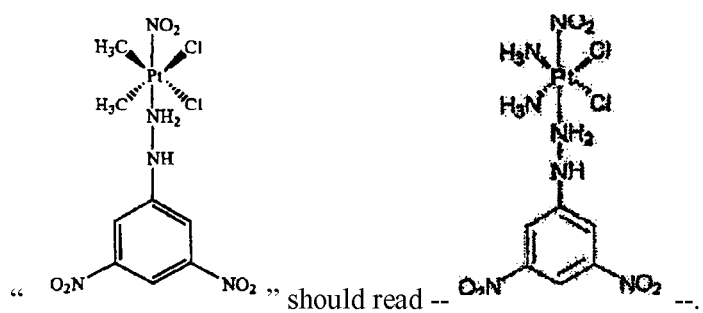

Columns 11 and 12,
Structure corresponding to CPA-44,

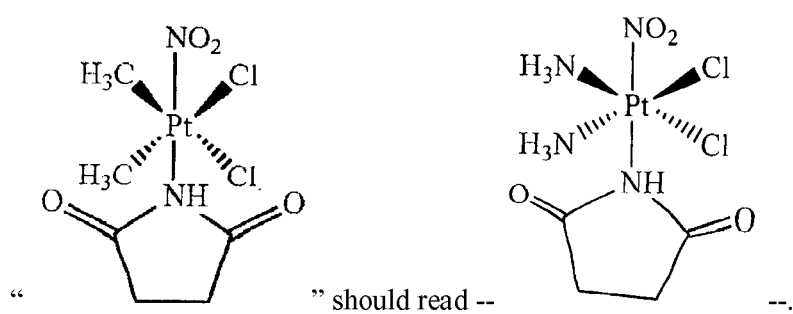

Columns 11 and 12,
Structure corresponding to CPA-45,

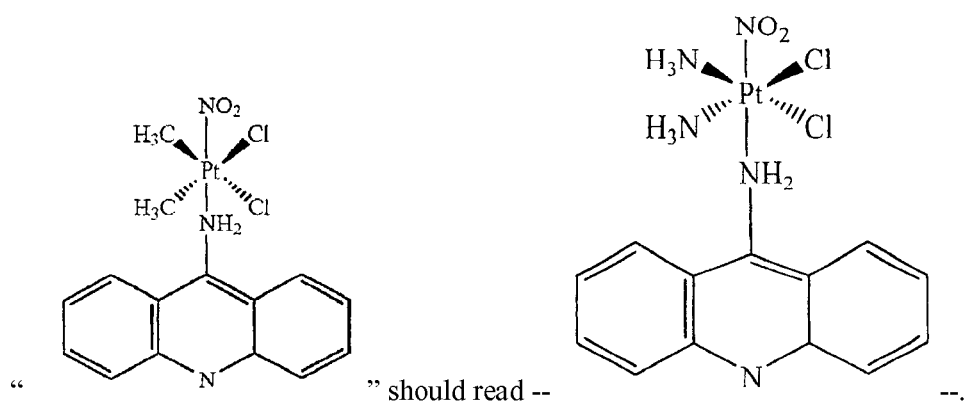

Columns 11 and 12,
Structure corresponding to CPA-46,
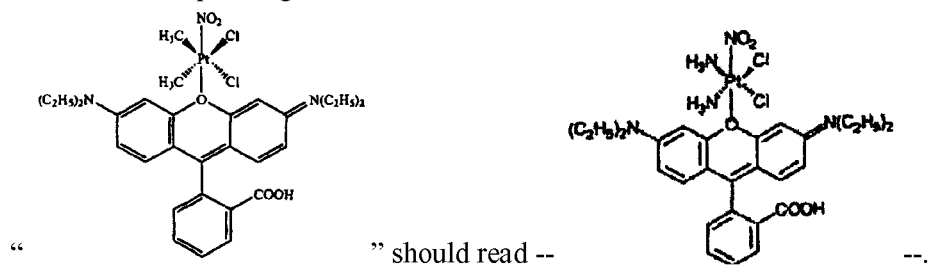
" should read -- --.
Column 13,
Designation for CPA-55, "Hydrocrotic acid" should read --Hydroorotic acid--.
Columns 15 and 16,
Structure corresponding to JP6,
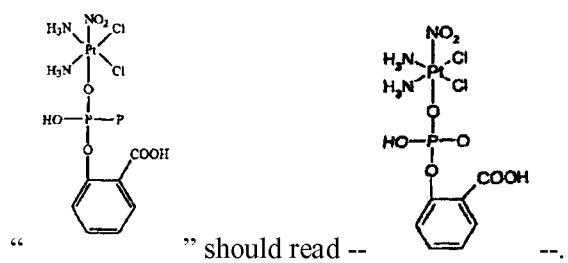
" should read -- --.
Column 25,
Structures corresponding to CPA-26 and CPA-27,
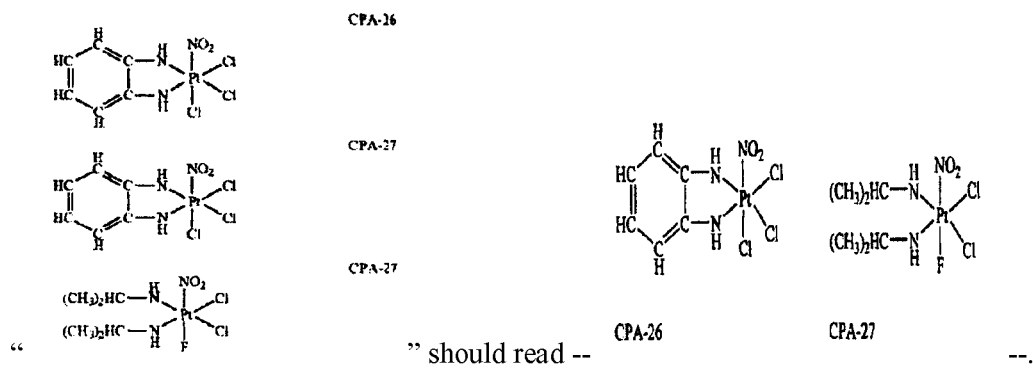
" should read -- --.

Column 34,
Structures corresponding to CPA-26 and CPA-27, " should read -- 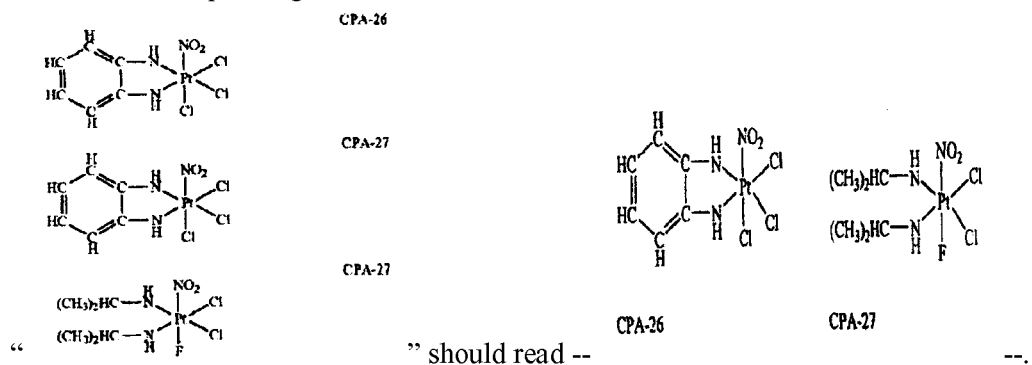 --.